(12) United States Patent
Choi et al.

(10) Patent No.: US 6,987,154 B2
(45) Date of Patent: Jan. 17, 2006

(54) SYNTHESIS OF A,B-ALTERNATING COPOLYMERS BY OLEFIN METATHESIS REACTIONS OF CYCLIC OLEFINS OR OLEFINIC POLYMERS WITH AN ACYCLIC DIENE

(75) Inventors: Tae-Lim Choi, Pasadena, CA (US); Choon Woo Lee, Pasadena, CA (US); Isaac M. Rutenberg, Pasadena, CA (US); Robert H. Grubbs, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 82 days.

(21) Appl. No.: 10/371,195

(22) Filed: Feb. 19, 2003

(65) Prior Publication Data

US 2003/0236377 A1 Dec. 25, 2003

Related U.S. Application Data

(60) Provisional application No. 60/359,055, filed on Feb. 19, 2002.

(51) Int. Cl.
*C08F 4/44* (2006.01)

(52) U.S. Cl. .................. 526/161; 526/172; 585/511; 585/514; 585/523; 560/205; 562/598

(58) Field of Classification Search ................ 526/161, 526/172; 585/643, 511, 514, 523; 560/205; 562/598

See application file for complete search history.

(56) References Cited

U.S. PATENT DOCUMENTS

| 5,731,383 A |   | 3/1998 | Nubel et al. |
| 5,750,815 A | * | 5/1998 | Grubbs et al. ............. 585/511 |
| 6,107,237 A |   | 8/2000 | Wagener et al. |
| 6,111,121 A |   | 8/2000 | Grubbs et al. |

FOREIGN PATENT DOCUMENTS

| WO | WO 02/079126 | 10/2002 |
| WO | WO 02/079127 | 10/2002 |
| WO | WO 02/079208 | 10/2002 |

OTHER PUBLICATIONS

Grubbs et al., Synthesis of A,B–Alternating Copolymers by Ring–Opening Insertion–Metathesis Polymerization, Angew. Chem. Int. Ed. 2002 vol. 41, No. 20.*
International Search Report, PCT/US03/05207, Jun. 2, 2003.
Scherman, Oren A., "Synthesis of Well–Defined Poly((vinyl alcohol)$_2$ –*alt*–methylene) via Ring– Opening Metathesis Polymerization," *Macromolecules*, 2002, vol. 35, No. 14, pp. 5366–5371.
Lee, Choon Woo et al, "Ring Expansion via Olefin Metathesis," *J. Am. Chem. Soc.*, 2002, vol. 124, No. 13, pp. 3224–3225.
Choi, Tae–Lim et al, "Synthesis of A,B–Alternating Copolymers by Ring–Opening–Insertion–Metathesis Polymerization," *Angew. Chem. Intl. Ed.*, 2002, vol. 41, No. 20, pp. 3839–3841.
Schultz, Laura G. et al, "Synthesis of Cored Dendrimers with Internal Cross–Links," *Angew. Chem. Intl. Ed.*, 2001, vol. 40, No. 10, pp. 1962–1966.
Lee, Choon Woo et al, "Formation of Macrocycles via Ring–Closing Olefin Metathesis," *J. Org. Chem.*, 2001, vol. 66, 7155–1758.
Fürstner, Alois, "Exploiting the Reversibility of Olefin Metathesis. Synthesis of Macrocyclic Trisubstituted Alkenes and (R,R)–(–)–Pyrenophorin," *Org. Lett.*, 2001, vol. 3, No. 3, pp. 449–451.
Garbaccio, Robert M. et al, "Efficient Asymmetric Synthesis of Radicol Dimethyl Ether: A Novel Application of Ring–Forming Olefin Metathesis," *Org. Lett.*, 2000, vol. 2, No. 20, pp. 3127–3129.
Lee, Choon Woo et al, "Stereoselectivity of Macrocyclic Ring–Closing Olefin Metathesis," *Org. Lett.*, 2000, vol. 2, No. 14, 2145–2147.
Roxburgh, Craig J., "The Syntheses of Large–Ring Compounds," *Tetrahedron*, 1995, vol. 51, No. 36, pp. 9767–9822.

* cited by examiner

*Primary Examiner*—Robert D. Harlan
(74) *Attorney, Agent, or Firm*—Dianne E. Reed; Mark L. Warzel; Reed Intellectual Property Law Group

(57) ABSTRACT

This invention relates generally to synthetic procedures that include the step of ring-opening metathesis of cyclic olefins and reaction with an acyclic diene co-reactant to produce regularly repeating A,B-alternating olefin polymers. The A,B-alternating polymers are produced by varying reaction conditions and/or reactant proportions and using only two types of olefin metathesis (ring-opening and cross) to provide regularly repeating ABAB . . . etc. polymers via ring-opening metathesis polymerization (ROMP). More particularly, the invention pertains to synthesis of A,B-alternating olefin polymers via olefin metathesis reactions using a Group 8 transition metal complex as the metathesis catalyst. Polymers provided herein have utility in a variety of fields, including not only polymer chemistry per se, but also in the pharmaceutical, biomedical, and packaging industries where the structure and properties of polymers need to be tightly controlled.

46 Claims, 1 Drawing Sheet

NMR spectra for a ROIMP product

SYNTHESIS OF A,B-ALTERNATING COPOLYMERS BY OLEFIN METATHESIS REACTIONS OF CYCLIC OLEFINS OR OLEFINIC POLYMERS WITH AN ACYCLIC DIENE

CROSS-REFERENCE TO RELATED APPLICATIONS

This application claims priority under 35 U.S.C. §119(e)(1) to Provisional U.S. Patent Application Ser. No. 60/359,055, filed Feb. 19, 2002. The disclosure of the aforementioned application is incorporated by reference in its entirety.

ACKNOWLEDGEMENT OF GOVERNMENT SUPPORT

The U.S. Government has certain rights in this invention pursuant to Grant No. CHE-9809856 awarded by the National Science Foundation.

TECHNICAL FIELD

This invention relates generally to the use of olefin metathesis in the synthesis of polymers, and more particularly relates to the synthesis of A,B-alternating olefin polymers via olefin metathesis reactions using a Group 8 transition metal complex as the metathesis catalyst. Polymers provided herein have utility in a variety of fields, including not only polymer chemistry per se, but also in the pharmaceutical, biomedical, and packaging industries where the structure and properties of polymers need to be tightly controlled.

BACKGROUND OF THE INVENTION

Olefin metathesis is an efficient reaction for the formation of carbon-carbon bonds by exchanging substituent groups on two olefin reactants. Certain ruthenium catalysts have helped to increase the practicality of using olefin metathesis for organic synthesis due to modified functional groups that have increased the tolerance of the complexes to air and moisture. However, highly active catalysts can be sensitive to some polar functional groups, while catalysts that are more stable with respect to polar functional groups can have diminished activity. Therefore, preferred metathesis catalysts are those that are more stable to functional groups while retaining substantially undiminished activity. There is also a need in the art for improved synthetic processes that can be carried out using such catalysts.

I. A,B-Alternating Copolymers and Derivatives

Interest in making well-defined linear polymers substituted with polar and/or functional groups has been spurred, in large part, by the widespread commercial utility of functionalized olefinic polymers. For example, ethylene-vinyl alcohol (EVOH) copolymers. EVOH copolymers, as a class, exhibit excellent barrier properties toward gases and hydrocarbons and have found use in the food packaging, biomedical, and pharmaceutical industries. See Lagaron et al. (2001) *Polym. Testing* 20:569–577, and Ramakrishnan (1991) *Macromolecules* 24:3753–3759.

Alternating copolymers are normally formed by step growth polymerization of AA-BB monomers and in some special chain-growth reactions (for example, in the synthesis of A,B-polyaminoacids). Although recent developments in ring-opening metathesis polymerization (ROMP) (e.g., U.S. Pat. No. 6,482,908) and acyclic-diene-metathesis polymerization (ADMET) (e.g., Wagener et al. (1990) *Makromol. Chem.* 191: 365–374, regarding ADMET polymerization of vinyl terminated oligo-octenylenes using a Lewis acid-free catalyst) have extended the versatility of both chain-growth and step-growth reactions, these metathesis polymerization reactions have not provided a general solution to alternating co-polymerization. Examples of alternating copolymers prepared by ROMP are rare as a result of the difficulty of finding systems in which there is an alternation in the affinity of the metal carbene for the monomers. Although ADMET is a step-growth polymerization, examples of alternating co-polymerization with two monomers by this mechanism have not been reported since most olefins studies have similar reactivity. Therefore, a general metathesis route toward A,B-alternating copolymers would open the way to the synthesis of new functional polymers.

The direct incorporation of polar functional groups along the backbone of linear polymers made via ring-opening metathesis polymerization is now possible due to the development of functional group-tolerant late transition metal olefin metathesis catalysts. Recently, Hillmyer et al. reported the ROMP of alcohol-, ketone-, halogen-, and acetate-substituted cyclooctenes with a ruthenium olefin metathesis catalyst (Hillmyer et al. (1995) *Macromolecules* 28: 6311–6316). However, the asymmetry of the substituted cyclooctene allowed for head-to-head (HH), head-to-tail (HT), and tail-to-tail (TT) coupling, yielding polymer with regiorandom placement of the functional groups. A similar problem was encountered by Chung et al., who reported the ROMP of a borane-substituted cyclooctene with an early transition metal catalyst followed by oxidation to yield an alcohol functionalized linear polymer (Ramakrishnan et al. (1990), supra). A solution to this regiorandom distribution of functional groups was reported by Valenti et al., who used the acyclic diene metathesis (ADMET) polymerization of an alcohol-containing symmetric diene (Valenti et al., supra; Schellekens et al. (2000) *J. Mol. Sci. Rev. Macromol. Chem. Phys.* C40:167–192)) However, the molecular weights of these polymers were restricted to <3×10$^4$ g/mol by ADMET, and their rich hydrocarbon content limits the barrier properties of the final EVOH copolymers (Lagaron et al., supra).

Accordingly, there is a need to provide an improved and efficient method for producing regioregular A,B-polymers. There is also a need for such regioregular olefin polymers that might be modified further by modifying functional groups in a regioregular or regiorandom manner. Another need is to provide a method that would permit producing derivatives from such A,B-regioregular polymers (e.g., A,C-polymers or AB,AC polymers in a regioregular or regiorandom manner) by direct insertion of monomer units into the polymer backbone.

II. Transition Metal Carbene Complexes as Metathesis Catalysts

Transition metal carbene complexes, particularly ruthenium and osmium carbene complexes, have been described as metathesis catalysts in U.S. Pat. Nos. 5,312,940, 5,342,909, 5,831,108, 5,969,170, 6,111,121, and 6,211,391 to Grubbs et al., assigned to the California Institute of Technology. The ruthenium and osmium carbene complexes disclosed in these patents all possess metal centers that are formally in the +2 oxidation state, have an electron count of 16, and are penta-coordinated. Such complexes have been disclosed as useful in catalyzing a variety of olefin metathesis reactions, including ROMP, ring closing metathesis ("RCM"), ADMET, ring-opening metathesis ("ROM"), and cross-metathesis ("CM" or "XMET") reactions. Examples of such catalysts are $(PCy_3)_2(Cl)_2Ru=CHPh$ (1) and $(IMesH_2)(PCy_3)(Cl)_2Ru=CHPh$ (2):

1:

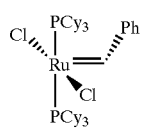

2:

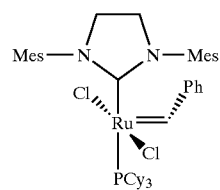

In the above molecular structures, "Mes" represents mesityl (2,4,6-trimethylphenyl), "Ph" is phenyl, and "Cy" is cyclohexyl.

Catalysts (1) and (2) have been shown to afford the ROMP of many substituted cyclic olefins. See, for example, Bielawski et al. (2000) *Angew. Chem., Int. Ed.* 39:2903–2906; Sanford et al. (2001) *J. Am. Chem. Soc.* 123:6543–6554; Amir-Ebrahimi et al. (2000) *Macromolecules* 33:717–724; and Hamilton et al. (2000) *J. Organomet. Chem* 606:8–12. Recent development of ruthenium catalysts, such as (2), coordinated with an N-heterocyclic carbene has allowed for the ROMP of low-strain cyclopentene and substituted cyclopentene. Bielawski et al., supra. The ROMP of a symmetric cyclopentene yields a regioregular polyalkene, as no difference exists between HH, HT, and TT couplings. Hence, the ROMP of alcohol- or acetate-disubstituted cyclopentene monomers was attempted (Scheme 1).

SCHEME 1

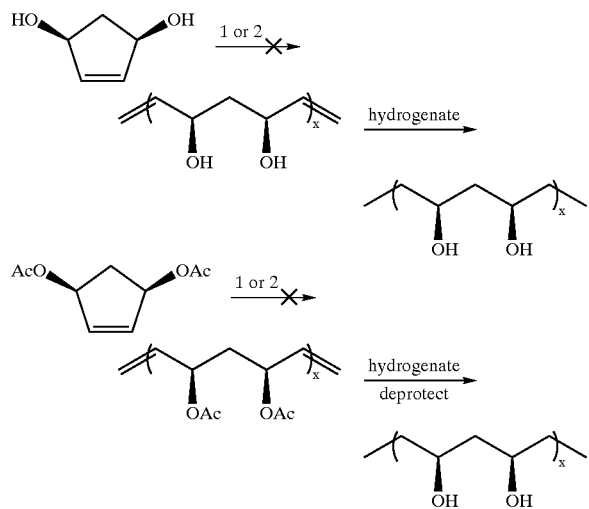

Unfortunately, neither catalyst (1) nor the more active (2) could afford the ROMP of these cyclopentene monomers under ordinary reaction conditions. Therefore, co-pending patent application Ser. No. 10/232,105, filed Aug. 29, 2002, entitled "Ring-Opening Metathesis Polymerization of Bridged Bicyclic and Polycyclic Olefins Containing Two or More Heteroatoms," provides a polymerization process utilizing protection and deprotection processes.

Accordingly, there is a need in the art for improved methods of synthesizing regioregular A,B-polymers and their derivatives, using catalysts that are tolerant of functional groups and a process that enables precise controls over the resulting products and structural distribution of functional groups in the molecules produced. Ideally, such a method would also be useful in the synthesis of regioregular and/or telechelic A,B-polymers. The invention is directed to such methods, and now provides a highly effective process using a transition metal carbene complex such as (1) or (2). The processes can be used to synthesize regioregular and/or telechelic A,B-polymers, in a manner that enables careful control over the macrocycles and polymer properties, as well as derivatives thereof.

SUMMARY OF THE INVENTION

The invention is directed, in part, to a method for synthesizing an alternating copolymer via sequential olefin metathesis reactions, comprising:

(a) synthesizing a polyolefin intermediate using a ring-opening metathesis polymerization (ROMP) reaction by contacting a cyclic olefin monomer with a catalytically effective amount of an olefin metathesis catalyst under reaction conditions effective to allow the ROMP reaction to occur; and (b) contacting the polyolefin intermediate with a diene monomer having two terminal olefinic groups under reaction conditions selected to effect metathesis insertion of the diene monomer into the backbone of the polyolefin intermediate.

The olefin metathesis catalyst for carrying out the aforementioned polymerization reaction is preferably a Group 8 transition metal complex having the structure of formula (I)

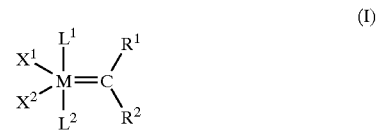

(I)

in which:

M is a Group 8 transition metal;

$L^1$ and $L^2$ are neutral electron donor ligands;

$X^1$ and $X^2$ are anionic ligands; and $R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $R^1$, and $R^2$ can be taken together to form a cyclic group, and further wherein any one or more of $X^1$, $X^2$, $L^1$, $L^2$, $R^1$, and $R^2$ may be attached to a support.

Preferred catalysts contain Ru or Os as the Group 8 transition metal, with Ru particularly preferred.

The catalysts having the structure of formula (I) are in one of two groups. In the first group, $L^1$ and $L^2$ are independently selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether. Exemplary ligands are trisubstituted phosphines. The first group of catalysts, accordingly, is exemplified by the ruthenium bisphosphine complex $(PCy_3)_2(Cl)_2Ru=CHPh$ (1)

1:

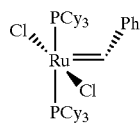

The catalysts of the second group are transition metal carbene complexes, preferably ruthenium carbene complexes, wherein $L^2$ is as defined above and $L^1$ is a carbene having the structure of formula (II)

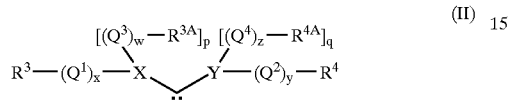

(II)

such that the complex has the structure of formula (IIA)

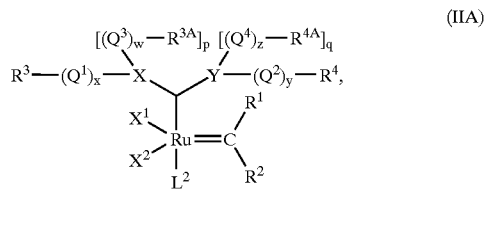

(IIA)

wherein:

$X^1$, $X^2$, $L^1$, $L^2$, $R^1$, and $R^2$ are as defined above;

X and Y are heteroatoms selected from N, O, S, and P;

p is zero when X is O or S, and p is 1 when X is N or P;

q is zero when Y is O or S, and q is 1 when Y is N or P;

$Q^1$, $Q^2$, $Q^3$, and $Q^4$ are independently selected from hydrocarbylene, substituted hydrocarbylene, heteroatom-containing hydrocarbylene, substituted heteroatom-containing hydrocarbylene, and —(CO)—, and further wherein two or more substituents on adjacent atoms within Q may be linked to form an additional cyclic group;

w, x, y, and z are independently zero or 1; and $R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl, wherein any two or more of $X^1$, $X^2$, $L^2$, $R^1$, $R^2$, $R^3$, $R^{3A}$, $R^4$, and $R^{4A}$ can be taken together to form a cyclic group, and further wherein any one or more of $X^1$, $X^2$, $L^2$, $R^1$, $R^2$, $R^3$, $R^{3A}$, $R^4$, and $R^{4A}$ may be attached to a support.

The second group of catalysts, accordingly, is exemplified by the ruthenium carbene complex $(IMesH_2)(PCy_3)(Cl)_2 Ru=CHPh$ (2):

2:

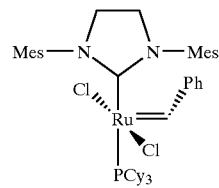

Additional transition metal carbene complexes useful as catalysts in conjunction with the present invention include, but are not limited to, neutral ruthenium or osmium metal carbene complexes containing metal centers that are formally in the +2 oxidation state, have an electron count of 16, are penta-coordinated, and are of the general formula (IIIA). Other preferred metathesis catalysts include, but are not limited to, cationic ruthenium or osmium metal carbene complexes containing metal centers that are formally in the +2 oxidation state, have an electron count of 14, are tetra-coordinated, and are of the general formula (IIIB). Still other preferred metathesis catalysts include, but are not limited to, neutral ruthenium or osmium metal carbene complexes containing metal centers that are formally in the +2 oxidation state, have an electron count of 18, are hexa-coordinated, and are of the general formula III(C).

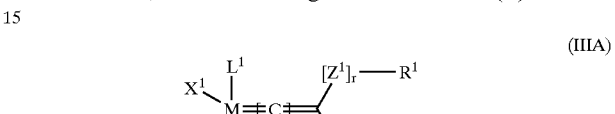

(IIIA)

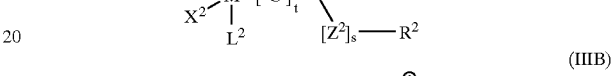

(IIIB)

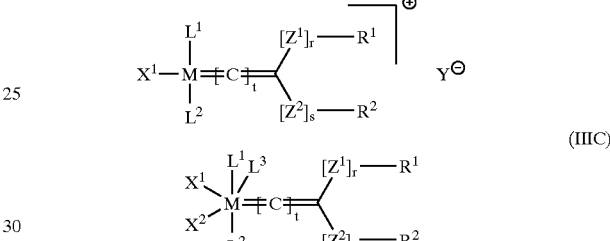

(IIIC)

In the foregoing structures, $X^1$, $X^2$, $L^1$, $L^2$, $R^1$, and $R^2$ are as defined previously, r and s are independently zero or 1, t is an integer in the range of zero to 5, Y is any noncoordinating anion, $Z^1$ and $Z^2$ are independently selected from —O—, —S—, —$NR^2$—, —$PR^2$—, —$P(=O)R^2$—, —$P(OR^2)$—, —$P(=O)(OR^2)$—, —C(=O)—, —C(=O)O—, —OC(=O)—, —OC(=O)O—, —S(=O)—, or —$S(=O)_2$—, and any two or more of $X^1$, $X^2$, $L^1$, $L^2$, $Z^1$, $Z^2$, $R^1$, and $R^2$ may be taken together to form a cyclic group, e.g., a multidentate ligand, and wherein any one or more of $X^1$, $X^2$, $L^1$, $L^2$, $Z^1$, $Z^2$, $R^1$, and $R^2$ may be attached to a support.

The cyclic olefin monomer has the structure of formula (IV)

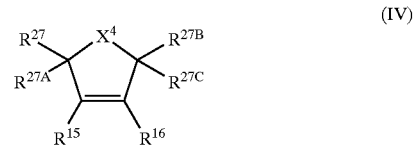

(IV)

wherein:

$X^4$ is a one-atom to five-atom linkage (with a "one-atom" linkage referring to a linkage that provides a single, optionally substituted spacer atom between the two adjacent carbon atoms, and a "five-atom" linkage, similarly, referring to a linkage that provides five optionally substituted spacer atoms between the two adjacent carbon atoms);

one of $R^{15}$ and $R^{16}$ is hydrogen and the other is selected from hydrogen, hydrocarbyl (e.g., $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, and $C_6$–$C_{24}$ aralkyl), substituted hydrocarbyl (e.g., substituted $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, and $C_6$–$C_{24}$ aralkyl), heteroatom-containing hydrocarbyl (e.g., heteroatom-containing $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, and $C_6$–$C_{24}$ aralkyl), substituted heteroatom-containing hydrocarbyl (e.g., substituted heteroatom-containing $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, and $C_6$–$C_{24}$ aralkyl), and -(L)$_v$-Fn wherein v is zero or 1, L is hydrocarbylene, substituted hydrocarbylene and/or heteroatom-containing hydrocarbylene, and Fn is a protected or unprotected functional group; and $R^{27}$, $R^{27A}$, $R^{27B}$, and $R^{27C}$ are independently selected from hydrogen, hydrocarbyl, substituted hydrocarbyl, heteroatom-containing hydrocarbyl, and substituted heteroatom-containing hydrocarbyl, and -(L)$_v$-Fn, and further wherein any two of $R^{27}$, $R^{27A}$, $R^{27B}$, and $R^{27C}$ may be taken together to form a cyclic structure, such that the olefin monomer is bicyclic, with the proviso that when the olefin monomer is bicyclic, then $X^4$ is a one-atom or two-atom linkage.

In one preferred embodiment, $R^{27A}$ and $R^{27C}$ are hydrogen, $R^{27}$ is -(L)$_v$-Fn wherein v is zero and -Fn is —$X^{3A}$—$(R^{18})_n$, and $R^{27B}$ is -(L)$_v$-Fn wherein v is zero and -Fn is —$X^3$—$(R^{17})_m$, and further wherein $X^3$ and $X^{3A}$ are directly or indirectly linked, in which case the cyclic olefin monomer has the structure of formula (VII)

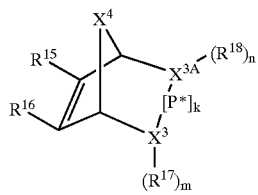

(VII)

in which:

$X^4$ is a one-atom or two-atom linkage;

$R^{15}$, and $R^{16}$ are as defined above;

$X^3$ and $X^{3A}$ are independently N, O, or S;

k is zero or 1;

m and n are independently zero or 1;

P* is a heteroatom-protecting group;

$R^{17}$ and $R^{18}$ are independently selected from hydrogen, hydrocarbyl, substituted hydrocarbyl, heteroatom-containing hydrocarbyl, substituted heteroatom-containing hydrocarbyl, and amino protecting groups, wherein $R^{17}$ and $R^{18}$ may be taken together to form a cyclic group., with the provisos that:

when $X^3$ is O or S, then m is zero;

when $X^{3A}$ is O or S, then n is zero;

when $X^3$ is N, then m is 1; and when $X^{3A}$ is N, then n is 1.

In another preferred embodiment, $R^{27A}$ and $R^{27C}$ of formula (IV) are hydrogen, in which case the cyclic olefin has the structure of formula (VIIa)

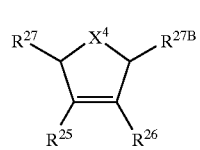

(VIIa)

wherein $X^4$, $R^{27}$, and $R^{27B}$ are as defined previously, and $R^{25}$ and $R^{26}$ are defined as for $R^{15}$ and $R^{16}$.

In the production of an alternating copolymer according to the invention, the ROMP reaction results in the synthesis of protected or unprotected, unsaturated regioregular polymer intermediates whenever the cyclic olefin monomer selected as the reactant is symmetrical about a central axis that bisects its olefinic bond. These unsaturated regioregular polymers can be reacted with a symmetrical diene monomer having two terminal olefinic groups under reaction conditions effective to effect metathesis insertion of the diene monomer into the backbone of the polyolefin intermediate and yield regioregular A,B alternating copolymers. Additionally, such copolymers can be further modified. For example, (a) protected groups on the copolymer product can be deprotected and optionally reacted further, (b) unsaturated bonds (including carbonyl groups) can be hydrogenated to give the corresponding saturated polymers and/or alcohols, and (c) different cyclic olefins can be reacted with the cyclic olefin residues on the polymer backbone by cross metathesis (insertion cross metathesis) to insert additional olefin monomer residues into the copolymer backbone and thereby a terpolymer, or alternatively to replace olefin monomer residues on the copolymer backbone and thereby yield a new regioregular copolymer. As an example, starting with monomers wherein $X^3$ and $X^{3A}$ are O, $X^4$ is methylene, and $R^{15}$ and $R^{16}$ are hydrogen, the polymer synthesized via ROMP is an unsaturated, protected analog of poly((vinyl alcohol)$_2$-alt-methylene)(MVOH), which can then be reacted with a symmetrical acyclic diene to produce a copolymer, which may then be hydrogenated and deprotected to give a regioregular copolymer comprising regioregular MVOH monomer residues.

The invention also provides, as novel compositions of matter, regioregular polymers that are synthesized using the methodology of the invention. The polymers are saturated or unsaturated, and, in a first embodiment, are comprised of recurring units having the alternating monomeric structure of formula (XV) corresponding to the cyclic olefin monomer and the monomeric structure of either formula (XVa) or (XVb) corresponding to the diene having two terminal olefinic groups:

wherein the monomeric structure corresponding to residue of the cyclic olefin is formula (XV) as follows:

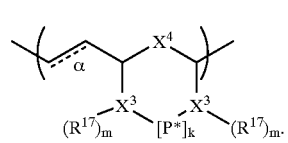

(XV)

wherein:

m, k, $X^3$, $R^{17}$, and P* are as defined with respect to the cyclic olefin monomers of formula (VII);

α is an optional double bond; and $X^4$ is a single-atom linkage having the structure $CR^{19}R^{20}$ wherein $R^{19}$ and $R^{20}$ are independently selected from hydrogen, substituted hydrocarbyl, heteroatom-containing hydrocarbyl, substituted heteroatom-containing hydrocarbyl, and functional groups; and wherein the monomeric structure residue corresponding to the diene having two terminal olefinic groups is either formula (XVa) or (XVb) as follows:

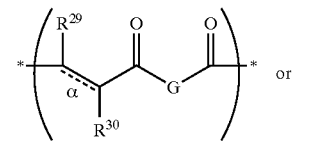
(XVa)

or

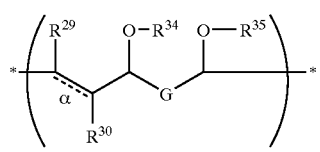
(XVb)

wherein:

α is an optional double bond;

$R^{29}$ and $R^{30}$ are each independently hydrogen or a substituent that does not interfere with metathesis, $R^{34}$ is $R^{35}$ are the same and are each hydrogen, a non-acyl alcohol protecting group, or an acyl group; and G is a hydrocarbylene linker group comprising 6–30 carbon atoms and the linker group is symmetrical about a central axis, wherein the carbon atoms of the linker group may be substituted or unsubstituted and the linker group may be interrupted by up to 6 hetero atoms selected from O, S and N, and wherein two or more substituents on the chain may be linked to form an additional cyclic group.

The copolymer may be telechelic, in which case the polymer terminates in two functional groups that enable further reaction.

In another embodiment, such copolymers may comprise alternating units of a hydrogenated monomeric structure corresponding to the hydrogenated cyclic olefin residue of formula (X) instead of the unsaturated cyclic olefin residue of formula (XV) as follows:

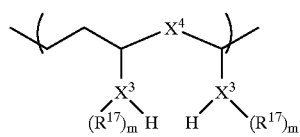
(X)

wherein $X^3$, $X^4$, $R^{17}$, and m are defined as for formula (XV), and further wherein the polymer may be telechelic and terminate in two functional groups, as described above with respect to copolymers comprising the formula (XV) structure.

In another embodiment, such copolymers may comprise alternating units of a monomeric structure corresponding to the hydrogenated cyclic olefin residue of formula (Xa) instead of the unsaturated cyclic olefin residue of formula (XV) as follows:

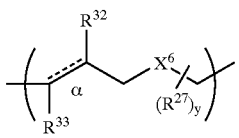
(Xa)

wherein y is 2 or 4, identical $R^{27}$ group pairs are attached symmetrically with respect to the $X^6$ group and are substituents on the two carbon atoms that are attached to the $X^6$ group having respect to the $X^6$ group is attached to $X^3$, $X^4$, $R^{17}$, and m are defined as for formula (XV), and further wherein the polymer may be telechelic and terminate in two functional groups, as described above with respect to copolymers comprising the formula (XV) structure.

wherein:

y is 0, 2 or 4;

identical $R^{27}$ group pairs are attached symmetrically with respect to the $X^6$ group and are substituents on the two carbon atoms that are attached to the $X^6$ group, and $R^{27}$ in each occurrence of symmetrical pair sets replace a hydrogen atom on each of the two carbon chains and each occurrence of pair sets is independently selected from hydrocarbyl, substituted hydrocarbyl, heteroatom-containing hydrocarbyl, substituted heteroatom-containing hydrocarbyl, and -(L)$_v$-Fn wherein v is zero or 1, L is hydrocarbylene, substituted hydrocarbylene and/or heteroatom-containing hydrocarbylene, and Fn is a functional group, wherein two $R^{27}$ pairs may collectively form two symmetrical carbonyl groups;

$R^{29}$ is a substituent identical to the $R^{32}$ substituent of formula XVa or XVb, and is hydrogen or a substituent that does not interfere with a metathesis reaction;

$R^{30}$ is a substituent identical to the $R^{31}$ substituent of formula XVa or XVb, and is hydrogen or a substituent that does not interfere with a metathesis reaction; and $X^6$ is a one-atom, two-atom, three-atom, four-atom or five atom linkage.

The invention represents a substantial improvement relative to prior synthetic methods that have been used to prepare regioregular copolymers, particularly regioregular copolymers comprising ethylene-(vinyl alcohol)(EVOH) monomeric units and analogous saturated copolymers, as well as regioregular copolymers having pendant heteroatom-containing functional groups. That is, prior methods for synthesizing such polymers resulted in random distribution of one of the monomer units along the copolymer's polymeric backbone with olefinic groups, hydroxyl groups or other functionalities being randomly distributed along the polymer backbone, and thereby limiting the utility of the polymers prepared. Earlier routes to polymers within the aforementioned class also resulted in branched and/or relatively low molecular weight copolymers (less than about 30,000). See, e.g., Ramakrishnan (1990), Ramakrishnan (1991), Valenti et al. (1998), Lagaron et al. (2001), and Schellekens et al. (2000) *J. Mol. Sci. Rev. Macromol. Chem. Phys.* C40: 167–192. By contrast, the present methodology allows for regioregular copolymer synthesis to take place in a controlled fashion over a large molecular weight range, such that the molecular weight, molecular weight distribution, polydispersity index (PDI), and linearity of the resulting copolymer product can be controlled. In addition, completely regioregular copolymers can be prepared by using a symmetric cyclic olefin as the monomeric substrate for the ROMP reaction, or by using a regioregular olefinic polymer and conducting a metathesis insertion copolymerization process with a diene having two terminal olefinic groups and thereby substituting the diene for olefinic groups on the regioregular polyolefin.

DETAILED DESCRIPTION OF THE INVENTION

Figure 1:
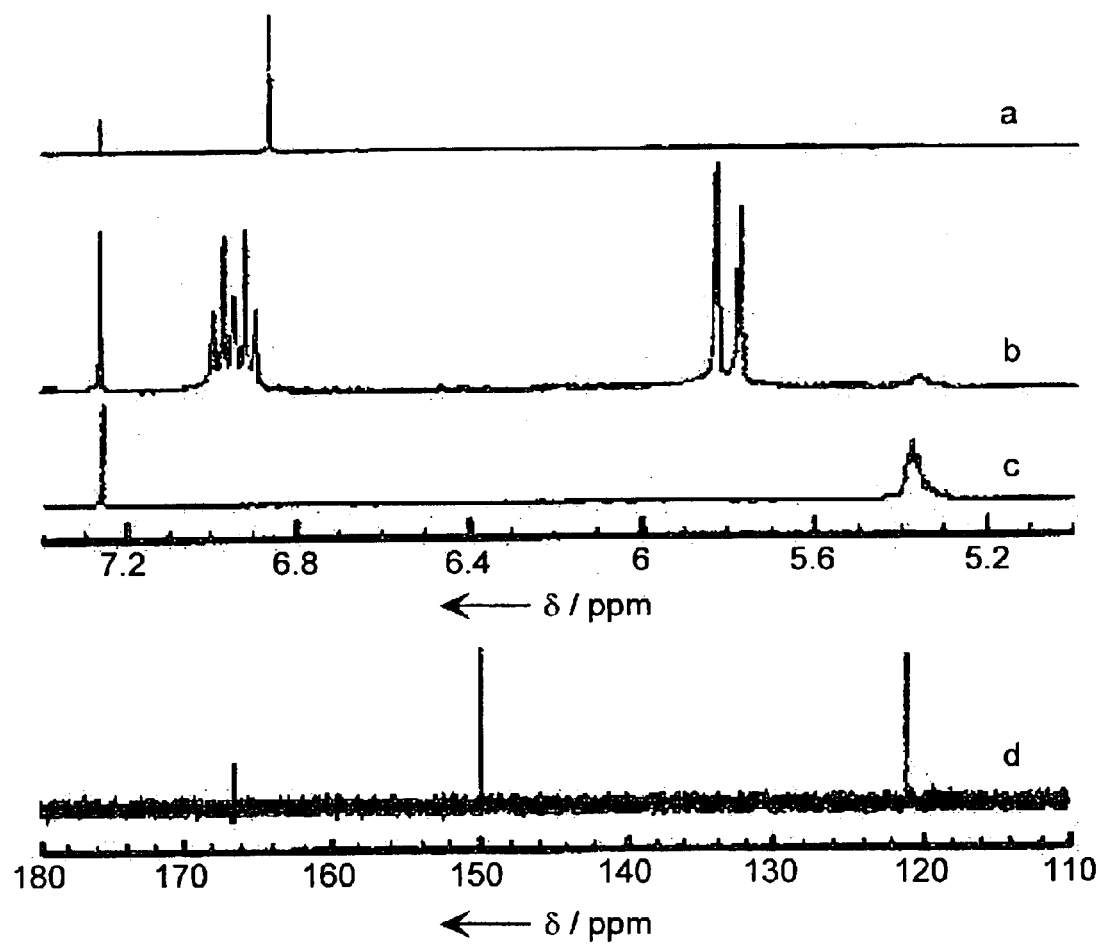
FIG. 1 provides NMR spectra a, b, c and d of ROIMP copolymers of Example 1 that were prepared according to the method of the invention. These NMR spectra illustrate the extent of A,B-alternation of monomers by $^1$H NMR and $^{15}$CNMR spectroscopic analysis, since olefinic protons for A,B-alternating units have a distinct chemical shift from the starting materials and homocoupled units. The NMR spectra a of FIG. 1 ($^1$H NMR) shows E-Acrylate dimers produce a sharp singlet at $\delta$=6.9 ppm), while NMR spectra c of FIG. 1 ($^1$H NMR) illustrates that polycycloalkenes display a multiplet at $\delta$=5.4 ppm. The NMR spectra b of FIG. 1 ($^1$H NMR) shows that A,B-alternating units produce a doublet of triplets at $\delta$=7.0 ppm and a doublet at $\delta$=5.8 ppm. Therefore, the extent of A,B-alternation in a copolymer can be easily calculated by integrating these peaks. The sharp coupling patterns demonstrate a highly uniform polymer structure with E olefin isomer (J=15.9 Hz). The NMR spectra d of FIG. 1 ($^{15}$CNMR) is spectroscopic analysis illustrating high A,B-alternation since it displays only two olefinic carbon peaks for carbon atoms $\alpha$ and $\beta$ to the carbonyl group.

I. Definitions and Nomenclature:

As used in the specification and the appended claims, the singular forms "a," "an," and "the" include plural referents unless the context clearly dictates otherwise. Thus, for example, reference to "a compound" encompasses a combination or mixture of different compounds as well as a single compound, reference to "a substituent" includes a single substituent as well as two or more substituent groups that may or may not be the same, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a linear, branched, or cyclic saturated hydrocarbon group typically although not necessarily containing 1 to about 20 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 20 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 20 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms and either one aromatic ring or 2 to 4 fused or linked aromatic rings, e.g., phenyl, naphthyl, biphenyl, and the like, with more preferred aryl groups containing 1 to 3 aromatic rings, and particularly preferred aryl groups containing 1 or 2 aromatic rings and 5 to 14 carbon atoms. "Substituted aryl" refers to an aryl moiety substituted with one or more substituent groups, and the terms "heteroatom-containing aryl" and "heteroaryl" refer to aryl in which at least one carbon atom is replaced with a heteroatom. Unless otherwise indicated, the terms "aromatic," "aryl," and "arylene" include heteroaromatic, substituted aromatic, and substituted heteroaromatic species.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-dienyl, and the like.

The terms "halo," "halide," and "halogen" are used in the conventional sense to refer to a chloro, bromo, fluoro, or iodo substituent. The terms "haloalkyl," "haloalkenyl," and "haloalkynyl" (or "halogenated alkyl," "halogenated alkenyl," and "halogenated alkynyl") refer to an alkyl, alkenyl, or alkynyl group, respectively, in which at least one of the hydrogen atoms in the group has been replaced with a halogen atom.

"Hydrocarbyl" refers to univalent hydrocarbyl radicals containing 1 to about 30 carbon atoms, preferably 1 to about 20 carbon atoms, more preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, and the term "hydrocarbylene" intends a divalent hydrocarbyl moiety containing 1 to about 30 carbon atoms, preferably 1 to about 20 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. Unless otherwise indicated, the terms "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage, or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc. It should be noted that a "heterocyclic" group or compound may or may not be aromatic, and further that "heterocycles" may be monocyclic, bicyclic, or polycyclic as described above with respect to the term "aryl."

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with a non-hydrogen substituent. Examples of such substituents include, without limitation, functional groups such as halide, hydroxyl, sulfhydryl, $C_1$–$C_{20}$ alkoxy, $C_2$–$C_{20}$ alkenyloxy, $C_2$–$C_{20}$ alkynyloxy, $C_5$–$C_{20}$ aryloxy, $C_2$–$C_{20}$ acyl (including $C_2$–$C_{20}$ alkylcarbonyl (—CO-alkyl) and $C_6$–$C_{20}$ arylcarbonyl (—CO-aryl)), acyloxy (—O-acyl), $C_2$–$C_{20}$ alkoxycarbonyl (—(CO)—O-alkyl), $C_6$–$C_{20}$ aryloxycarbonyl (—(CO)—O-aryl), halocarbonyl (—CO)—X where X is halo), $C_2$–$C_{20}$ alkyl-carbonato (—O—(CO)—O-alkyl), $C_6$–$C_{20}$ arylcarbonato (—O—(CO)—O-aryl), carboxy (—COOH), carboxylato (—COO$^-$), carbamoyl (—(CO)—NH$_2$), mono-($C_1$–$C_{20}$ alkyl)-substituted carbamoyl (—(CO)—NH($C_1$–$C_{20}$ alkyl)), di-($C_1$–$C_{20}$ alkyl)-substituted carbamoyl (—(CO)—N($C_1$–$C_{20}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—C≡N), cyanato (—O—C≡N), formyl (—(CO)—H), thioformyl (—(CS)—H), amino (—NH$_2$), mono- and di-($C_1$–$C_{20}$ alkyl)-substituted amino, mono- and di-($C_5$–$C_{20}$ aryl)-substituted amino, $C_2$–$C_{20}$ alkylamido (—NH—(CO)-alkyl), $C_6$–$C_{20}$ arylamido (—NH—(CO)-aryl), imino (—CR=NH where R=hydrogen, $C_1$–$C_{20}$ alkyl, $C_5$–$C_{20}$ aryl, $C_6$–$C_{24}$ alkaryl, $C_6$–$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$–$C_{20}$ alkylsulfanyl (—S-alkyl; also termed "alkylthio"), arylsulfanyl (—S-aryl; also termed "arylthio"), $C_1$–$C_{20}$ alkylsulfinyl (—(SO)-alkyl), $C_5$–$C_{20}$ arylsulfinyl (—(SO)-aryl), $C_1$–$C_{20}$ alkylsulfonyl (—SO$_2$-alkyl), $C_5$–$C_{20}$ arylsulfonyl (—SO$_2$-aryl), thiocarbonyl (=S), boryl (—BH$_2$), borono (—B(OH)$_2$), boronato (—B(OR)$_2$ where R is alkyl or other hydrocarbyl), phospho (—PO$_2$), phosphino (—PH$_2$), silyl (—SiR$_3$ wherein R is hydrogen or hydrocarbyl), silyloxy (—O-silyl), silanyl (—NR-silyl, where R is hydrogen or hydrocarbyl), stannyl, or germyl; and the hydrocarbyl moieties $C_1$–$C_{20}$ alkyl (preferably $C_1$–$C_{18}$ alkyl, more preferably $C_1$–$C_{12}$ alkyl, most preferably $C_1$–$C_6$ alkyl), $C_2$–$C_{20}$ alkenyl (preferably $C_2$–$C_{18}$ alkenyl, more preferably $C_2$–$C_{12}$ alkenyl, most preferably $C_2$–$C_6$ alkenyl), $C_2$–$C_{20}$ alkynyl (preferably $C_2$–$C_{18}$ alkynyl, more preferably $C_2$–$C_{12}$ alkynyl, most preferably $C_2$–$C_6$ alkynyl), $C_5$–$C_{20}$ aryl (preferably $C_5$–$C_{14}$ aryl), $C_6$–$C_{24}$ alkaryl (preferably $C_6$–$C_{18}$ alkaryl), and $C_6$–$C_{24}$ aralkyl (preferably $C_6$–$C_{18}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Analogously, the term "optionally substituted alkyl, alkenyl and alkynyl" is to be interpreted as "optionally substituted alkyl, optionally substituted alkenyl and optionally substituted alkynyl," and a "bridged bicyclic or polycyclic olefin monomer" is to be interpreted as a "bridged bicyclic olefin monomer" or a "bridged polycyclic olefin monomer."

The term "regioregular polymer" is used to refer to a polymer with a regular arrangement of the "connectivity" between the monomer units.

The term "regioregular copolymer" is used to refer the connectivity of monomeric units (e.g., monomeric unit A and monomeric unit B) along the polymeric backbone wherein the copolymer is composed of the two connected in a regularly alternating arrangement pattern ( . . . ABABAB . . . ) along its polymeric backbone. In one preferred type of regioregular copolymer each of the two monomeric units is also symmetrical along a central axis of the monomer unit the "connectivity" between the monomer units The term "telechelic" is used in the conventional sense to refer to a macromolecule, e.g., a polymer or copolymer, that is capped by at least one reactive end group. Preferred telechelic compounds herein are regioregular copolymers having two terminal functional groups each capable of undergoing further reaction.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

II. Catalysts:

The metathesis reactions of the invention are carried out catalytically, using a Group 8 transition metal complex as the catalyst. These transition metal carbene complexes include a metal center in a +2 oxidation state, have an electron count of 16, and are penta-coordinated. The complexes are represented by the structure of formula (I)

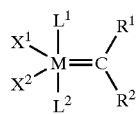

(I)

wherein the various substituents are as follows:

M, which serves as the transition metal center in the +2 oxidation state, is a Group 8 transition metal, particularly ruthenium or osmium. In a particularly preferred embodiment, M is ruthenium.

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$–$C_{20}$ alkyl, $C_5$–$C_{20}$ aryl, $C_1$–$C_{20}$ alkoxy, $C_5$–$C_{20}$ aryloxy, $C_2$–$C_{20}$ alkoxycarbonyl, $C_6$–$C_{20}$ aryloxycarbonyl, $C_2$–$C_{20}$ acyl, $C_2$–$C_{20}$ acyloxy, $C_1$–$C_{20}$ alkylsulfonato, $C_5$–$C_{20}$ arylsulfonato, $C_1$–$C_{20}$ alkylsulfanyl, $C_5$–$C_{20}$ arylsulfanyl, $C_1$–$C_{20}$ alkylsulfinyl, or $C_5$–$C_{20}$ arylsulfinyl. Optionally, $X^1$ and $X^2$ may be substituted with one or more moieties selected from $C_1$–$C_{12}$ alkyl, $C_1$–$C_{12}$ alkoxy, $C_5$–$C_{20}$ aryl, and halide, which may, in turn, with the exception of halide, be further substituted with one or more groups selected from halide, $C_1$–$C_6$ alkyl, $C_1$–$C_6$ alkoxy, and phenyl. In more preferred embodiments, $X^1$ and $X^2$ are halide, benzoate, $C_2$–$C_6$ acyl, $C_2$–$C_6$ alkoxycarbonyl, $C_1$–$C_6$ alkyl, phenoxy, $C_1$–$C_6$ alkoxy, $C_1$–$C_6$ alkylsulfanyl, aryl, or $C_1$–$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments, $X^1$ and $X^2$ are each chloride.

$R^1$ and $R^2$ are independently selected from hydrogen, hydrocarbyl (e.g., $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, $C_6$–$C_{24}$ aralkyl, etc.), substituted hydrocarbyl (e.g., substituted $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, $C_6$–$C_{24}$ aralkyl, etc.), heteroatom-containing hydrocarbyl (e.g., heteroatom-containing $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, $C_6$–$C_{24}$ aralkyl, etc.), and substituted heteroatom-containing hydrocarbyl (e.g., substituted heteroatom-containing $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, $C_6$–$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5 to 8, ring atoms. $R^1$ and $R^2$ may also together form a vinylidene moiety or an analog thereof, as discussed infra with respect to catalysts having the structure of formula (IIIA).

In preferred catalysts, the $R^1$ substituent is hydrogen and the $R^2$ substituent is selected from $C_1$–$C_{20}$ alkyl, $C_2$–$C_{20}$ alkenyl, and $C_5$–$C_{20}$ aryl. More preferably, $R^2$ is phenyl, vinyl, methyl, isopropyl, or t-butyl, optionally substituted with one or more moieties selected from $C_1$–$C_6$ alkyl, $C_1$–$C_6$ alkoxy, phenyl, and a functional group Fn as defined in part (I) of this section. Still more preferably, $R^2$ is phenyl or vinyl substituted with one or more moieties selected from methyl, ethyl, chloro, bromo, iodo, fluoro, nitro, dimethylamino, methyl, methoxy, and phenyl. In the most preferred embodiments, the $R^2$ substituent is phenyl or —C=C(CH$_3$)$_2$.

$L^1$ and $L^2$ are neutral electron donor ligands. $L^1$ may or may not be linked to $R^1$, and $L^2$ may or may not be linked to $R^2$. Examples of suitable $L^2$ moieties include, without limitation, phosphine, sulfonated phosphine, phosphite, phosphinite, phosphonite, arsine, stibine, ether (including cyclic ethers), amine, amide, imine, sulfoxide, carboxyl, nitrosyl, pyridine, substituted pyridine (e.g., halogenated pyridine), imidazole, substituted imidazole (e.g., halogenated imidazole), pyrazine (e.g., substituted pyrazine), and thioether. In more preferred embodiments, $L^2$ is a phosphine of the formula $PR^5R^6R^7$, where $R^5$, $R^6$, and $R^7$ are each independently aryl or $C_1$–$C_{10}$ alkyl, particularly primary alkyl, secondary alkyl, or cycloalkyl. In the most preferred embodiments, $L^1$ is tricyclohexylphosphine, tricyclopentylphosphine, triisopropylphosphine, triphenylphosphine, diphenylmethylphosphine, or phenyldimethylphosphine, with tricyclohexylphosphine and tricyclopentylphosphine particularly preferred.

It should be emphasized that any two or more (typically two, three, or four) of $X^1$, $X^2$, $L^1$, $L^2$, $R^1$, and $R^2$ can be taken together to form a cyclic group, as disclosed, for example, in U.S. Pat. No. 5,312,940 to Grubbs et al. When any of $X^1$, $X^2$, $L^1$, $L^2$, $R^1$, and $R^2$ are linked to form cyclic groups, those cyclic groups may be five- or six-membered rings, or may comprise two or three five- or six-membered rings, which may be either fused or linked. The cyclic groups may be aliphatic or aromatic, and may be heteroatom-containing and/or substituted, as explained in part (I) of this section.

The cyclic group may, in some cases, form a bidentate ligand or a tridentate ligand. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$—, —As(Ph)$_2$ CH$_2$CH$_2$As (Ph$_2$)—, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$—, and —OC(CH$_3$)$_2$(CH$_3$)$_2$CO—. Preferred bidentate ligands are —P(Ph)$_2$ CH$_2$CH$_2$P(Ph)$_2$— and —P(CH$_3$)$_2$(CH$_2$)$_2$P (CH$_3$)$_2$—. Tridentate ligands include, but are not limited to, (CH$_3$)$_2$ NCH$_2$CH$_2$P(Ph)CH$_2$CH$_2$N(CH$_3$)$_2$. Other preferred tridentate ligands are those in which any three of $X^1$, $X^2$, $L^1$, $L^2$, $R^1$, and $R^2$ (e.g., $X^1$, $L^1$, and $L^2$) are taken together to be cyclopentadienyl, indenyl, or fluorenyl, each optionally substituted with $C_2$–$C_{20}$ alkenyl, $C_2$–$C_{20}$ alkynyl, $C_1$–$C_{20}$ alkyl, $C_5$–$C_{20}$ aryl, $C_1$–$C_{20}$ alkoxy, $C_2$–$C_{20}$ alkenyloxy, $C_2$–$C_{20}$ alkynyloxy, $C_5$–$C_{20}$ aryloxy, $C_2$–$C_{20}$ alkoxycarbonyl, $C_1$–$C_{20}$ alkylthio, $C_1$–$C_{20}$ alkylsulfonyl, or $C_1$–$C_{20}$ alkylsulfinyl, each of which may be further substituted with $C_1$–$C_6$ alkyl, halide, $C_1$–$C_6$ alkoxy or with a phenyl group optionally substituted with halide, $C_1$–$C_6$ alkyl, or $C_1$–$C_6$ alkoxy. More preferably, in compounds of this type, X, $L^1$, and $L^2$ are taken together to be cyclopentadienyl or indenyl, each optionally substituted with vinyl, $C_1$–$C_{10}$ alkyl, $C_5$–$C_{20}$ aryl, $C_1$–$C_{10}$ carboxylate, $C_2$–$C_{10}$ alkoxycarbonyl, $C_1$–$C_{10}$ alkoxy, or $C_5$–$C_{20}$ aryloxy, each optionally substituted with $C_1$–$C_6$ alkyl, halide, $C_1$–$C_6$ alkoxy or with a phenyl group optionally substituted with halide, $C_1$–$C_6$ alkyl or $C_1$–$C_6$ alkoxy. Most preferably, X, $L^1$ and $L^2$ may be taken together to be cyclopentadienyl, optionally substituted with vinyl, hydrogen, methyl, or phenyl. Tetradentate ligands include, but are not limited to O$_2$C(CH$_2$)$_2$P(Ph)(CH$_2$)$_2$P(Ph)(CH$_2$)$_2$ CO$_2$, phthalocyanines, and porphyrins.

Complexes wherein $L^2$ and $R^2$ are linked, for example, include the following:

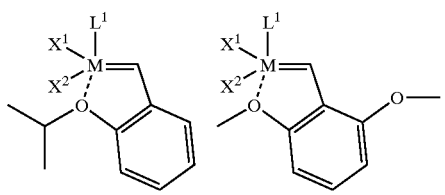

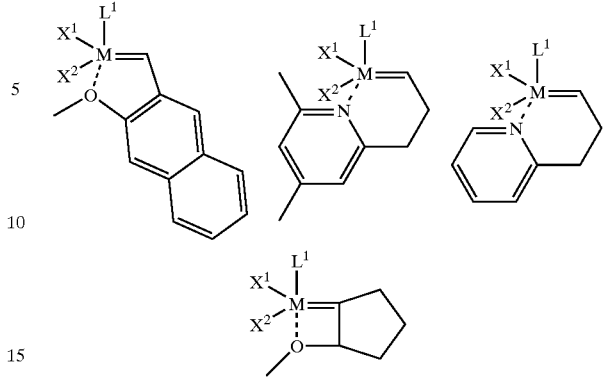

In a first group of catalysts, $L^1$ is as defined for $L^2$, and, in this embodiment, $L^1$ and $L^2$ will generally, although not necessarily, be the same. In these catalysts, $L^1$ and $L^2$ are typically phosphines of the formula PR$^5$R$^6$R$^7$, where R$^5$, R$^6$, and R$^7$ are as defined earlier herein. As above, the most preferred $L^1$ and $L^2$ ligands, in this first catalyst group, are selected from tricyclohexylphosphine, tricyclopentylphosphine, triisopropylphosphine, triphenylphosphine, diphenylmethylphosphine, and phenyldimethylphosphine, with tricyclohexylphosphine and tricyclopentylphosphine particularly preferred. These catalysts are, accordingly, exemplified by ruthenium bisphosphine complexes such as (PCy$_3$)$_2$(Cl)$_2$Ru=CHPh (1).

In a second group of catalysts, the complexes are ruthenium carbene complexes, wherein $L^1$ has the structure of formula (II)

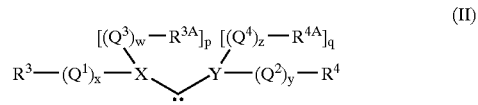

such that the complexes have the structure of formula (IIA)

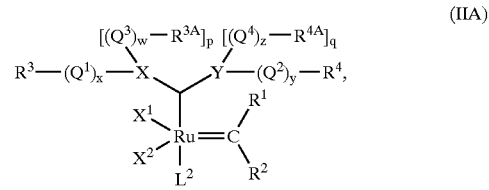

wherein the substituents are as follows:

X and Y are heteroatoms typically selected from N, O, S, and P. Since O and S are divalent, p is necessarily zero when X is O or S, and q is necessarily zero when Y is O or S. However, when X is N or P, then p is 1, and when Y is N or P, then q is 1. In a preferred embodiment, both X and Y are N.

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Preferably, w, x, y, and z are all zero. Further, two or more substituents on adjacent atoms within Q may be linked to form an additional cyclic group.

$R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl.

In addition, any two or more of $X^1$, $X^2$, $L^2$, $R^1$, $R^2$, $R^3$, $R^{3A}$, $R^4$, and $R^{4A}$ can be taken together to form a cyclic group, and any one or more of $X^1$, $X^2$, $L^2$, $R^1$, $R^2$, $R^3$, $R^{3A}$, $R^4$, and $R^{4A}$ may be attached to a support, as explained above with respect to complexes of formula (I).

Preferably, $R^{3A}$ and $R^{4A}$ are linked to form a cyclic group, such that the complexes of this embodiment have the structure of formula (V)

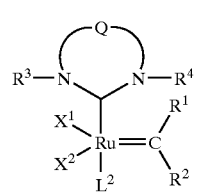

(V)

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to five cyclic groups. Q is often, although again not necessarily, a two-atom linkage or a three-atom linkage, e.g., —CH$_2$—CH$_2$—, —CH(Ph)—CH(Ph) where Ph is phenyl; =CR—N=, giving rise to an unsubstituted (when R=H) or substituted (R=other than H) triazolyl group; and —CH$_2$—SiR$_2$—CH$_2$— (where R is H, alkyl, alkoxy, etc.).

In a more preferred embodiment, Q is a two-atom linkage having the structure —CR$^8$R$^9$—CR$^{10}$R$^{11}$— or —CR$^8$=CR$^{10}$—, preferably —CR$^8$R$^9$—CR$^{10}$R$^{11}$—, in which case the complex has the structure of formula (Va)

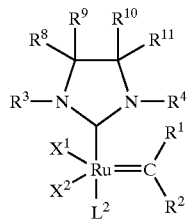

(Va)

wherein $R^8$, $R^9$, $R^{10}$, and $R^{11}$ are independently selected from hydrogen, hydrocarbyl, substituted hydrocarbyl, heteroatom-containing hydrocarbyl, substituted heteroatom-containing hydrocarbyl, and functional groups as defined in part (I) of this section. Examples of functional groups here include carboxyl, $C_1$–$C_{20}$ alkoxy, $C_5$–$C_{20}$ aryloxy, $C_2$–$C_{20}$ alkoxycarbonyl, $C_2$–$C_{20}$ alkoxycarbonyl, $C_2$–$C_{20}$ acyloxy, $C_1$–$C_{20}$ alkylthio, $C_5$–$C_{20}$ arylthio, $C_1$–$C_{20}$ alkylsulfonyl, and $C_1$–$C_{20}$ alkylsulfinyl, optionally substituted with one or more moieties selected from $C_1$–$C_{10}$ alkyl, $C_1$–$C_{10}$ alkoxy, $C_5$–$C_{20}$ aryl, hydroxyl, sulfhydryl, formyl, and halide. Alternatively, any two of $R^8$, $R^9$, $R^{10}$, and $R^{11}$ may be linked together to form a substituted or unsubstituted, saturated or unsaturated ring structure, e.g., a $C_4$–$C_{12}$ alicyclic group or a $C_5$ or $C_6$ aryl group, which may itself be substituted, e.g., with linked or fused alicyclic or aromatic groups, or with other substituents.

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and have the structure (VI)

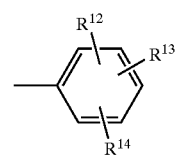

(VI)

in which $R^{12}$, $R^{13}$, and $R^{14}$ are each independently hydrogen, $C_1$–$C_{20}$ alkyl, substituted $C_1$–$C_{20}$ alkyl, $C_1$–$C_{20}$ heteroalkyl, substituted $C_1$–$C_{20}$ heteroalkyl, $C_5$–$C_{20}$ aryl, substituted $C_5$–$C_{20}$ aryl, $C_5$–$C_{20}$ heteroaryl, $C_5$–$C_{30}$ aralkyl, $C_5$–$C_{30}$ alkaryl, or halide. Preferably, $R^{12}$, $R^{13}$, and $R^{14}$ are each independently hydrogen, $C_1$–$C_{10}$ alkyl, $C_1$–$C_{10}$ alkoxy, $C_5$–$C_{14}$ aryl, substituted $C_5$–$C_{14}$ aryl, or halide. More preferably, $R^3$ and $R^4$ are mesityl, diisopinocamphenyl, or 2,4,2',6'-tetramethylbiphenylyl, and most preferably, $R^3$ and $R^4$ are mesityl.

Examples of such catalysts include, but are not limited to, the following:

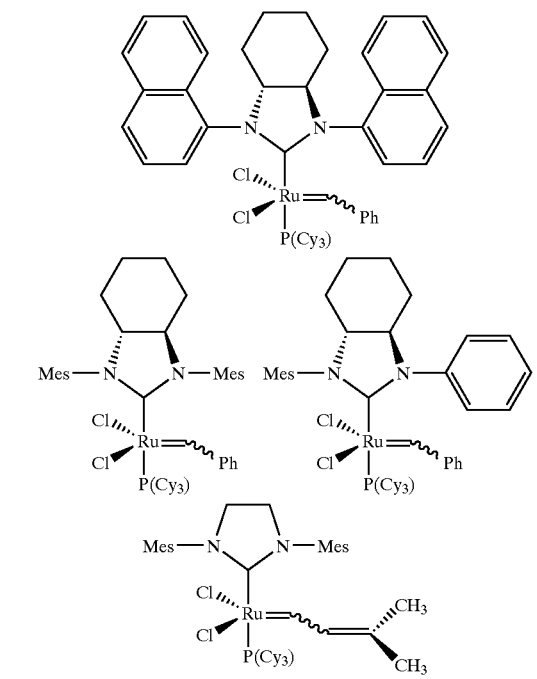

-continued

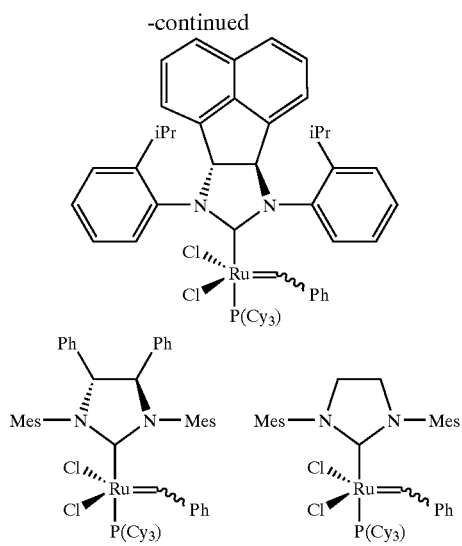

In the foregoing molecular structures, "Mes" represents mesityl (2,4,6-trimethylphenyl), "iPr" is isopropyl, "Ph" is phenyl, and "Cy" is cyclohexyl.

Additional transition metal carbene complexes include, but are not limited to:

neutral ruthenium or osmium metal carbene complexes containing metal centers that are formally in the +2 oxidation state, have an electron count of 16, are penta-coordinated, and are of the general formula (IIIA);

cationic ruthenium or osmium metal carbene complexes containing metal centers that are formally in the +2 oxidation state, have an electron count of 14, are tetra-coordinated, and are of the general formula (IIIB); and neutral ruthenium or osmium metal carbene complexes containing metal centers that are formally in the +2 oxidation state, have an electron count of 18, are hexa-coordinated, and are of the general formula III(C)

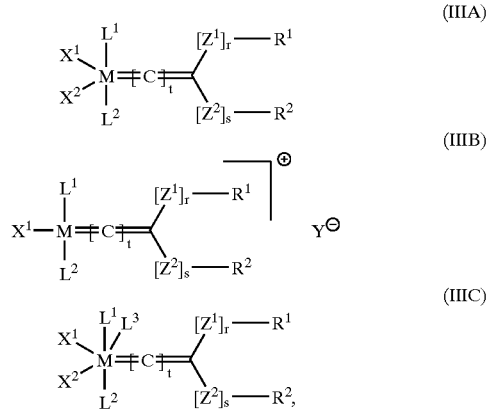

wherein $X^1$, $X^2$, $L^1$, $L^2$, $R^1$, and $R^2$ are as defined previously, r and s are independently zero or 1, t is an integer in the range of zero to 5, Y is any noncoordinating anion (e.g., a halide ion), $Z^1$ and $Z^2$ are independently selected from —O—, —S—, —$NR^2$—, —$PR^2$—, —P(=O)$R^2$—, —P(O$R^2$)—, —P(=O)(O$R^2$)—, —C(=O)—, —C(=O)O—, —OC(=O)—, —OC(=O)O—, —S(=O)—, or —S(=O)$_2$—, and any two or more of $X^1$, $X^2$, $L^1$, $L^2$, $Z^1$, $Z^2$, $R^1$, and $R^2$ may be taken together to form a cyclic group, e.g., a multidentate ligand, and wherein any one or more of $X^1$, $X^2$, $L^1$, $L^2$, $Z^1$, $Z^2$, $R^1$, and $R^2$ may be attached to a support. As understood in the field of catalysis, suitable solid supports may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect, if indirect, typically through a functional group on a support surface.

The transition metal complexes used as catalysts herein can be prepared by several different methods, such as those described by Schwab et al. (1996) *J. Am. Chem. Soc.* 118:100–110, Scholl et al. (1999) *Org. Lett.* 6:953–956, Sanford et al. (2001) *J. Am. Chem. Soc.* 123:749–750, U.S. Pat. No. 5,312,940 and U.S. Pat. No. 5,342,909. Also see U.S. patent application Ser. No. 10/115,581 to Grubbs, Morgan, Benitez, and Louie, filed Apr. 2, 2002, for "One-Pot Synthesis of Group 8 Transition Metal Carbene Complexes Useful as Olefin Metathesis Catalysts," commonly assigned herewith to the California Institute of Technology.

The transition metal complexes used as catalysts herein, particularly the ruthenium carbene complexes, have a well-defined ligand environment that enables flexibility in modifying and fine-tuning the activity level, stability, solubility and ease of recovery of these catalysts. See, e.g., U.S. Pat. No. 5,849,851 to Grubbs et al. In addition, the solubility of the carbene complexes may be controlled by proper selection of either hydrophobic or hydrophilic ligands, as is well known in the art. The desired solubility of the catalyst will largely be determined by the solubility of the reaction substrates and reaction products. It is well known in the art to design catalysts whose solubility is distinguishable from that of the reaction substrates and products, thereby facilitating recovery of the catalyst from the reaction mixture.

III. Synthesis of Copolymers via ROIMP:

In one embodiment, the invention is a method for synthesizing a copolymer via an olefin metathesis insertion reaction, comprising contacting a polyolefin with a diene monomer having two terminal olefinic groups in the presence of a catalytically effective amount of an olefin metathesis catalyst under reaction conditions effective to provide metathesis insertion of the diene monomer into the backbone of the polyolefin, wherein the concentration of the diene in the reaction medium is from 0.2 to 2 molar. In a preferred embodiment the invention utilizes a regioregular polyolefin and the insertion process provides a regioregular alternating copolymer.

In a process wherein the above method is a second step of a two-step process, the first step of the process may utilize a method for synthesizing an olefinic polymer using a ROMP reaction, comprising contacting an olefin monomer with a catalytically effective amount of an olefin metathesis catalyst under reaction conditions effective to allow the ROMP reaction to occur, wherein the olefin monomer contains a plurality of heteroatoms, at least two of which are directly or indirectly linked to each other. By "directly" linked is meant that the two heteroatoms are linked to each other through a direct, covalent bond. By "indirectly" linked is meant that one or more spacer atoms are present between the heteroatoms; generally, the "indirect" linkage herein refers to the presence of a single atom (that may or may not be substituted) to which each heteroatom is linked through a direct covalent bond. Preferably, the olefin monomer contains one double bond, and the two heteroatoms are symmetrically positioned with respect to any axis that is perpendicular to the double bond.

As an example, the cyclic olefin monomer has the structure of formula (IV)

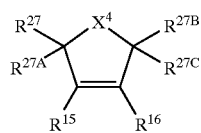

(IV)

wherein the various substituents are as follows:

$X^4$ is a one-atom to five-atom linkage. In a preferred embodiment, and when the monomer is bicyclic (e.g., when $R^{27}$ and $R^{27B}$ are linked), then X is a one-atom or two-atom linkage, i.e., a linkage that introduces one or two optionally substituted spacer atoms between the two carbon atoms to which $X^4$ is bound. Generally, although not necessarily, $X^4$ will be of the formula —$CR^{19}R^{20}$—$(X^5)_h$— wherein h is zero or 1, $X^5$ is $CR^{21}R^{22}$, O, S, or $NR^{23}$, and $R^{19}$, $R^{20}$, $R^{21}$, $R^{22}$, and $R^{23}$ are independently selected from hydrogen, hydrocarbyl (e.g., $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, $C_6$–$C_{24}$ aralkyl, $C_1$–$C_{20}$ alkyl, $C_5$–$C_{20}$ aryl, $C_5$–$C_{30}$ aralkyl, or $C_5$–$C_{30}$ alkaryl), substituted hydrocarbyl (e.g., substituted $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, $C_6$–$C_{24}$ aralkyl, $C_1$–$C_{20}$ alkyl, $C_5$–$C_{20}$ aryl, $C_5$–$C_{30}$ aralkyl, or $C_5$–$C_{30}$ alkaryl), heteroatom-containing hydrocarbyl (e.g., $C_1$–$C_{20}$ heteroalkyl, $C_5$–$C_{20}$ heteroaryl, heteroatom-containing $C_5$–$C_{30}$ aralkyl, or heteroatom-containing $C_5$–$C_{30}$ alkaryl), substituted heteroatom-containing hydrocarbyl (e.g., substituted $C_1$–$C_{20}$ heteroalkyl, $C_5$–$C_{20}$ heteroaryl, heteroatom-containing $C_5$–$C_{30}$ aralkyl, or heteroatom-containing $C_5$–$C_{30}$ alkaryl) and protected and unprotected functional groups such as those enumerated in part (I) of this section. Protected functional groups include, by way of example, protected hydroxyl groups, wherein the protecting group is t-butyl silyl (TBS), acyl, or tetrahydropyranyl.

When h is 1, preferred linkages are wherein $X^5$ is $CR^{21}R^{22}$, giving rise to a substituted or unsubstituted ethylene moiety. That is, when $R^{19}$, $R^{20}$, $R^{21}$, and $R^{22}$ are hydrogen, then $X^4$ is ethylene. When h is zero, the linkage is substituted or unsubstituted methylene, and a particularly preferred linkage within this group is methylene per se (i.e., when $R^{19}$ and $R^{20}$ are both hydrogen).

One of $R^{15}$ and $R^{16}$ is hydrogen and the other is selected from hydrogen, hydrocarbyl (e.g., $C_1$–$C_{20}$ alkyl, $C_5$–$C_{20}$ aryl, $C_5$–$C_{30}$ aralkyl, or $C_5$–$C_{30}$ alkaryl), substituted hydrocarbyl (e.g., substituted $C_1$–$C_{20}$ alkyl, $C_5$–$C_{20}$ aryl, $C_5$–$C_{30}$ aralkyl, or $C_5$–$C_{30}$ alkaryl), heteroatom-containing hydrocarbyl (e.g., $C_1$–$C_{20}$ heteroalkyl, $C_5$–$C_{20}$ heteroaryl, heteroatom-containing $C_5$–$C_{30}$ aralkyl, or heteroatom-containing $C_5$–$C_{30}$ alkaryl), substituted heteroatom-containing hydrocarbyl (e.g., substituted $C_1$–$C_{20}$ heteroalkyl, $C_5$–$C_{20}$ heteroaryl, heteroatom-containing $C_5$–$C_{30}$ aralkyl, or heteroatom-containing $C_5$–$C_{30}$ alkaryl), and -(L)$_v$-Fn wherein v is zero or 1, L is hydrocarbylene, substituted hydrocarbylene and/or heteroatom-containing hydrocarbylene, and Fn is a protected or unprotected functional group. Preferred functional groups include, without limitation, hydroxyl, sulfhydryl, $C_1$–$C_{20}$ alkoxy, $C_5$–$C_{20}$ aryloxy, $C_2$–$C_{20}$ acyloxy, $C_2$–$C_{20}$ alkoxycarbonyl, $C_6$–$C_{20}$ aryloxycarbonyl, halocarbonyl, carboxy, carbamoyl, mono-($C_1$–$C_{20}$ alkyl)-substituted carbamoyl, di-($C_1$–$C_{20}$ alkyl)-substituted carbamoyl, mono-($C_5$–$C_{20}$ aryl)-substituted carbamoyl, cyano, cyanato, formyl, amino, mono- and di-substituted amino, nitro, nitroso, sulfo, $C_1$–$C_{20}$ alkylsulfanyl, $C_5$–$C_{20}$ arylsulfanyl, $C_1$–$C_{20}$ alkylsulfonyl, $C_5$–$C_{20}$ arylsulfonyl, $C_1$–$C_{20}$ alkylsulfinyl, $C_5$–$C_{20}$ arylsulfinyl, boryl, borono, boronato, phospho, phosphino, silyl, and silyloxy. Most preferably, $R^{15}$ and $R^{16}$ are hydrogen.

$R^{27}$, $R^{27A}$, $R^{27B}$, and $R^{27C}$ are independently selected from hydrogen, hydrocarbyl (e.g., $C_1$–$C_{20}$ alkyl, $C_5$–$C_{20}$ aryl, $C_5$–$C_{30}$ aralkyl, or $C_5$–$C_{30}$ alkaryl), substituted hydrocarbyl (e.g., substituted $C_1$–$C_{20}$ alkyl, $C_5$–$C_{20}$ aryl, $C_5$–$C_{30}$ aralkyl, or $C_5$–$C_{30}$ alkaryl), heteroatom-containing hydrocarbyl (e.g., $C_1$–$C_{20}$ heteroalkyl, $C_5$–$C_{20}$ heteroaryl, heteroatom-containing $C_5$–$C_{30}$ aralkyl, or heteroatom-containing $C_5$–$C_{30}$ alkaryl), substituted heteroatom-containing hydrocarbyl (e.g., substituted $C_1$–$C_{20}$ heteroalkyl, $C_5$–$C_{20}$ heteroaryl, heteroatom-containing $C_5$–$C_{30}$ aralkyl, or heteroatom-containing $C_5$–$C_{30}$ alkaryl), and -(L)$_v$-Fn wherein v, L and Fn are defined above. Additionally, any two or more of $R^{27}$, $R^{27A}$, $R^{27B}$, and $R^{27C}$ can be taken together to form a cyclic group, which may be, for example, five- or six-membered rings, or two or three five- or six-membered rings, which may be either fused or linked. The cyclic groups may be aliphatic or aromatic, and may be heteroatom-containing and/or substituted.

One group of such cyclic olefins are those of formula (IV) wherein $R^{27A}$ and $R^{27C}$ are hydrogen, $R^{27}$ is -(L)$_v$-Fn wherein v is zero and -Fn is —$X^{3A}$—$(R^{18})_n$, and $R^{27B}$ is -(L)$_v$-Fn wherein v is zero and -Fn is —$X^3$—$(R^{17})_m$, and further wherein $X^3$ and $X^{3A}$ are directly or indirectly linked. In this embodiment, then, the cyclic olefin monomer has the structure of formula (VII)

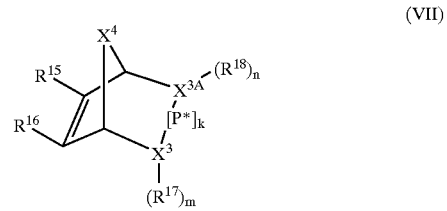

(VII)

in which:

$X^4$, $R^{15}$, and $R^{16}$ are as defined above with respect to olefin monomers of formula (IV);

$X^3$ and $X^{3A}$ are independently N, O, or S;

k is zero or 1;

m and n are independently zero or 1;

P* is a heteroatom-protecting group;

$R^{17}$ and $R^{18}$ are independently selected from hydrogen, hydrocarbyl, substituted hydrocarbyl, heteroatom-containing hydrocarbyl, substituted heteroatom-containing hydrocarbyl, and amino protecting groups, wherein $R^{17}$ and $R^{18}$ may be taken together to form a cyclic group., with the provisos that:

when $X^3$ is O or S, then m is zero;

when $X^{3A}$ is O or S, then n is zero;

when $X^3$ is N, then m is 1; and when $X^{3A}$ is N, then n is 1.

Preferred olefin monomers having the structure of formula (VII) are those wherein the various substituents are as follows:

P* is a protecting group, particularly a heteroatom-protecting group. P* must be inert with respect to the reagents and reaction conditions used for polymerization as well as the reagents and conditions used for any subsequent reactions (e.g., hydrogenation, as described infra), but must be removable following completion of ROMP and any subsequent polymer modification reactions. As may be deduced from the structure of formula (VII) and the above definitions, P* is a protecting group for functional groups having the structure —$X^3$H (or —$X^{3A}$H), wherein $X^3$ (or $X^{3A}$) is O or S. Accordingly, when $X^3$ and $X^{3A}$ are O or S, P* will be a protecting group "linkage" used to protect 1,3-diols and 1,3-dithiols, respectively. A number of such bifunctional protecting groups are known in the art and described, for example, in Greene et al., *Protective Groups in Organic Synthesis*, 3$^{rd}$ Ed. (New York: Wiley, 1999). In the present method, a preferred protecting group for 1,3-diols (i.e., cyclic olefins of formula (VII) wherein $X^3$ and $X^{3A}$ is OH) is —Si($R^{24}$)$_2$— wherein $R^{24}$ is tertiary alkyl, preferably tertiary lower alkyl, e.g., t-butyl, and the deprotecting agent normally used is tetrabutylammonium fluoride. Other preferred protecting groups for 1,3-diols are cyclic acetals and ketals, such as methylene acetal, ethylidene acetal, t-butylmethylidene ketal, 1-t-butylethylidene ketal, 1-phenylethylidene ketal, cyclopentylidene ketal, cyclohexylidene ketal, benzylidene acetal, and acetonide (isopropylidene ketal), with acetonide particularly preferred. Such groups are typically removed via acid hydrolysis, preferably, although not necessarily, at an elevated temperature. With acetonide-protected 1,3-diols, deprotection may be achieved not only via acid hydrolysis, but also using other means, e.g., with boron trichloride or bromine. Preferred protecting groups for 1,3-dithiols (i.e., cyclic olefins of formula (VII) wherein $X^3$ is SH) are methylene, benzylidene (both removable with sodium/ammonia), and isopropylidene (removable with mercury (II) chloride).

$R^{17}$ and $R^{18}$ are independently selected from hydrogen, hydrocarbyl, substituted hydrocarbyl, heteroatom-containing hydrocarbyl, substituted heteroatom-containing hydrocarbyl, and amino protecting groups. $R^{17}$ and $R^{18}$ may also be linked to form a protecting group linking the nitrogen atoms to which they are attached. Removal of such protecting groups and regeneration of the unprotected amino moieties can be carried out using the method of Bøgevig et al. (2002) *Angew. Chem. Int. Ed.* 41:1790–1793.

Representative olefin monomers of formula (VII) in which $X^3$ and $X^{3A}$ are different are those wherein k and m are zero, n is 1, $X^3$ is O, $X^{3A}$ is N, and $R^{18}$ is an amino protecting group, e.g., a carboxylic acid ester such as —(CO)—O-t-Bu. When $X^4$ is methylene, and $R^{15}$ and $R^{16}$ are hydrogen, the monomer is 2-oxa-3-aza-bicyclo[2.2.1]hept-5-ene-3-carboxylic acid t-butyl ester, having the structure (VIIB)

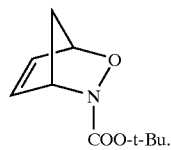

(VIIB)

The monomer can be readily synthesized using a hetero-Diels Alder reaction. See Mulvihill et al. (1998), *J. Org. Chem.* 63:3357. Following polymerization, deprotection can be achieved using the method of Vogt et al. (1998) *Tetrahedron* 54:1317–1348.

Representative olefin monomers of formula (VII) in which $X^3$ and $X^{3A}$ are the same are those wherein $X^3$ and $X^{3A}$ are O, k is 1, m, and n are zero, and P* is a protecting group for 1,3-diols. When $X^4$ is methylene, and $R^{15}$ and $R^{16}$ are hydrogen, an exemplary monomer is 3,3-di-tert-butyl-2,4-dioxa-3-sila-bicyclo[3.2.1]oct-6-ene (olefin compound (3) hereinafter).

As another example of useful cyclic olefin monomers, $R^{27A}$ and $R^{27C}$ of formula (IV) are hydrogen, in which case the cyclic olefin has the structure of formula (VIIA)

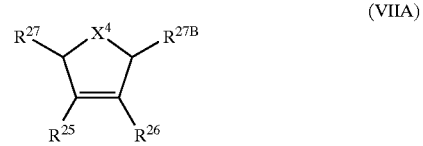

(VIIA)

wherein $X^4$, $R^{27}$, and $R^{27B}$ are as defined previously, and $R^{25}$ and $R^{26}$ are defined as for $R^{15}$ and $R^{16}$.

Exemplary monocyclic olefins encompassed by formula (VIIA) (i.e., olefins wherein $R^{27}$ and $R^{27B}$ are not linked) include, without limitation, cyclopentene, 3-methylcyclopentene, 4-methylcyclopentene, 3-t-butyldimethylsilyloxycyclopentene, 4-t-butyldimethylsilyloxycyclopentene, cyclohexene, 3-methylcyclohexene, 4-methyl-cyclohexene, 3-t-butyldimethylsilyloxycyclohexene, 4-t-butyldimethylsilyloxycyclohexene, cycloheptene, 3-methylcycloheptene, 4-methylcycloheptene, 5-methylcycloheptene, 3-t-butyldimethylsilyloxycycloheptene, 4-t-butyldimethylsilyloxycycloheptene, 5-t-butyldimethylsilyloxycycloheptene, cyclooctene, 3-methylcyclooctene, 4-methylcyclooctene, 5-methylcyclooctene, 3-t-butyldimethyl-silyloxycyclooctene, 4-t-butyldimethylsilyloxycyclooctene, 5-t-butyldimethylsilyloxycyclooctene, cyclononene, 3-methylcyclononene, 4-methylcyclononene, 5-methylcyclononene, 6-methylcyclo-nonene, 3-t-butyldimethylsilyloxycyclononene, 4-t-butyldimethylsilyloxycyclononene, 5-t-butyl-dimethylsilyloxycyclononene, 6-t-butyldimethylsilyloxycyclononene, cyclodecene, 3-methylcyclo-decene, 4-methylcyclodecene, 5-methylcyclodecene, 6-methylcyclodecene, 3-t-butyldimethylsilyloxycyclodecene, 4-t-butyldimethylsilyloxycyclononene, 5-t-butyldimethylsilyloxycyclodecene, 6-t-butyldimethylsilyloxycyclodecene, cycloundecene, 3-methylcycloundecene, 4-methylcycloundecene, 5-methylcycloundecene, 6-methylcycloundecene, 7-methylcycloundecene, 3-t-butyldimethylsilyloxycycloundecene, 4-t-butyldimethylsilyloxycycloundecene, 5-t-butyldimethylsilyloxy-cycloundecene, 6-t-butyldimethylsilyloxycycloundecene, 7-t-butyldimethylsilyloxycycloundecene, cyclododecene, 3-methylcyclododecene, 4-methylcyclododecene, 5-methylcyclododecene, 6-methyl-cyclododecene, 7-methylcyclododecene, 3-t-butyldimethylsilyloxycyclododecene, 4-t-butyldimethylsilyloxycyclododecene, 5-t-butyldimethylsilyloxycyclododecene, 6-t-butyldimethylsilyloxycyclododecene, and 7-t-butyldimethylsilyloxycyclododecene.

More preferred cyclic olefins are members selected from the group cyclopentene, 3-methylcyclopentene, 3-t-butyldimethylsilyloxycyclopentene, cyclohexene, 4-methylcyclohexene, 4-t-butyldimethylsilyloxycyclohexene, cycloheptene, cyclooctene, 5-methylcyclooctene, 5-t-butyldimethylsilyloxycyclooctene, cyclononene, and cyclododecene.

Regioregular polymers can be readily synthesized using monomers of formula (VII) in which $X^{3A}$ is identical to $X^3$, $X^4$ is methylene or substituted methylene (i.e., $CR^{19}R^{20}$ wherein $R^{19}$ and $R^{20}$ are as defined earlier herein), $R^{18}$ is identical to $R^{17}$, and n is identical to m, such that the synthesized polymer is an unsaturated regioregular polymer comprised of recurring units having the structure of formula (VIII)

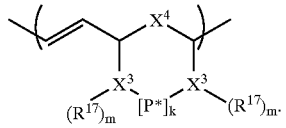

(VIII)

It will be appreciated that when $X^3$ is O or S, such that m is zero and k is 1, the unsaturated regioregular polymer is comprised of recurring units having the structure of formula (VIIIA)

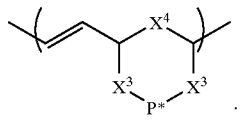

(VIIIA)

The polymerization reaction is generally carried out in an inert atmosphere by dissolving a catalytically effective amount of an olefin metathesis catalyst (preferably a Group 8 transition metal complex of formula (I)) in a solvent, and adding the bicyclic or polycyclic olefin monomer (preferably a monomer of formula (VII)), optionally dissolved in a solvent, to the catalyst solution. Preferably, the reaction is agitated (e.g., stirred). The progress of the reaction can be monitored by standard techniques, e.g., nuclear magnetic resonance spectroscopy. Examples of solvents that may be used in the polymerization reaction include organic, protic, or aqueous solvents that are inert under the polymerization conditions, such as aromatic hydrocarbons, chlorinated hydrocarbons, ethers, aliphatic hydrocarbons, alcohols, water, or mixtures thereof. Preferred solvents include benzene, toluene, p-xylene, methylene chloride, 1,2-dichloroethane, dichlorobenzene, chlorobenzene, tetrahydrofuran, diethylether, pentane, methanol, ethanol, water, or mixtures thereof. More preferably, the solvent is benzene, toluene, p-xylene, methylene chloride, 1,2-dichloroethane, dichlorobenzene, chlorobenzene, tetrahydrofuran, diethylether, pentane, methanol, or ethanol. Most preferably, the solvent is toluene or 1,2-dichloroethane. The solubility of the polymer formed in the polymerization reaction will depend on the choice of solvent and the molecular weight of the polymer obtained. Under certain circumstances, no solvent is needed.

Reaction temperatures can range from about 0° C. to 100° C., and are preferably in the range of about 25° C. to 75° C., and the reaction time will generally be in the range of about 12 to 48 hours. The molar ratio of cyclic olefin monomer to the catalyst is selected based on the desired molecular weight of the polymer, the desired polydispersity index (PDI, defined as $M_w$: $M_n$), and the activity of the particular catalyst. As the present method is a controlled polymerization, there is a substantially linear relationship between molecular weight and the monomer/catalyst ratio (see Example 1 and FIGS. 2A and 2B). With more active catalysts, the polymerization reaction can proceed with far less catalyst, so that the [monomer]/[catalyst] ratio can be extraordinarily high (see Example 2), reducing overall cost significantly. However, to achieve a lower PDI, i.e., a PDI of at most about 1.4, a less active catalyst is desirable, in which case the [monomer]/[catalyst] ratio will be lower (see Example 1). In general, the transition metal carbene complexes of formula (IIA) are more active than the bisphosphine catalysts of formula (I) (i.e., complexes wherein $L^1$ and $L^2$ are tri-substituted phosphines or analogous ligands, as explained in part (II)). Accordingly, the former catalysts are preferred for minimizing catalyst loading and achieving a broader molecular weight distribution, i.e., a PDI of 2 or more, while the latter catalysts are preferred when higher catalyst loadings are acceptable and a narrower molecular weight distribution, i.e., a PDI of 1.4 or less, is desired. Achieving an $M_n$ of over 200,000 will generally require a molar ratio of monomer to catalyst of 500:1 or more (see Example 2).

In order to provide a saturated regioregular polymer, the unsaturated polymer of formula (VIII) is hydrogenated using conventional reagents and conditions, e.g., using tosyl hydrazide as described in Example 3. The resulting hydrogenated polymer is comprised of recurring units having the structure of formula (IX)

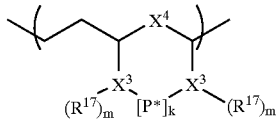

(IX)

When the unsaturated polymer is comprised of recurring units having the structure of formula (VIIIA), the hydrogenated polymer, correspondingly, is comprised of recurring units having the structure of formula (IXA)

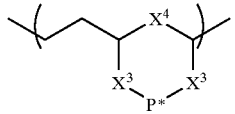

(IXA)

Deprotection of (IX) is then effected as described above, using a reagent effective to provide a deprotected regioregular polymer comprised of recurring units having the formula (X)

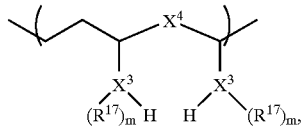

(X)

which, when $X^3$ is O or S, such that m is zero and k is 1, have the structure of formula (XA)

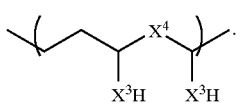

(XA)

The methodology of the invention also extends to the synthesis of telecheic polymers via a ROMP reaction. Telechelic polymers, as is well known, are macromolecules with one or more reactive end groups. Telechelic polymers are useful materials for chain extension processes, block copolymer synthesis, reaction injection molding, and network formation. Uses for telechelic polymers and syntheses thereof are described in Goethals, *Telechelic Polymers: Synthesis and Applications* (CRC Press: Boca Raton, Fla., 1989).

For most applications, highly functionalized telechelic polymers are preferred. Thus, it is desirable that the catalyst used to form the telechelic polymer be stable in the presence of functional groups. The Group 8 transition metal complexes described in part (II) are, in fact, stable with respect to a wide variety of functional groups, as described, for example, in U.S. Pat. Nos. 5,312,940, 5,342,909, 5,917,071, 5,969,170, 6,111,121, and 6,313,332 to Grubbs et al., and in U.S. patent application Ser. No. 10/114,418 to Grubbs et al., filed Apr. 1, 2002, for "Cross-Metathesis Reaction of Functionalized and Substituted Olefins Using Group 8 Transition Metal Carbene Complexes as Metathesis Catalysts," all of which are commonly assigned herewith to the California Institute of Technology.

In implementing the present methodology to synthesize telechelic polymers, the ROMP reaction is carried out in the presence of acyclic olefins act that as chain transfer agents to regulate the molecular weight of polymers produced. When α,ω-difunctional olefins are employed as chain transfer agents, difunctional telechelic polymers can be synthesized, and such difunctional olefins are the preferred chain transfer agents herein. When carrying out a ROMP reaction using a symmetric, α,ω-difunctional olefin as a chain transfer agent, the propagating alkylidene generated during the ring-opening metathesis process is terminated with a functional group, and the new functionally substituted alkylidene reacts with a monomer to initiate a new chain. This process preserves the number of active catalyst centers and leads to symmetric telechelic polymers with a functionality that approaches 2.0. The only polymer end groups that do not contain residues from the chain transfer agent are those from the initiating alkylidene and the end-capping reagent. In principle, these end groups could be chosen to match the end group from the chain transfer agent. See U.S. Pat. No. 5,880,231 to Grubbs et al.

In general, the α,ω-difunctional olefin that serves as the chain transfer agent (CTA) has the structure of formula (XI)

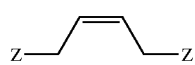

(XI)

wherein Z comprises a functional group selected from halide, hydroxyl, sulfhydryl, $C_2$–$C_{20}$ acyloxy, $C_2$–$C_{20}$ alkoxycarbonyl, $C_6$–$C_{20}$ aryloxycarbonyl, halocarbonyl, $C_2$–$C_{20}$ alkylcarbonato, $C_6$–$C_{20}$ arylcarbonato, carboxy, carbamoyl, mono-substituted carbamoyl, disubstituted carbamoyl, thiocarbamoyl, carbamido, cyano, cyanato, formyl, thioformyl, amino, mono-substituted amino, di-substituted amino, imino, alkylimino, arylimino, nitro, nitroso, sulfo, $C_1$–$C_{20}$ alkylsulfanyl, $C_5$–$C_{20}$ arylsulfanyl, $C_1$–$C_{20}$ alkylsulfinyl, $C_5$–$C_{20}$ arylsulfinyl, $C_1$–$C_{20}$ alkylsulfonyl, arylsulfonyl, boryl, phosphono, phospho, and phosphino. Preferred Z groups are selected from hydroxyl, sulfhydryl, $C_2$–$C_{12}$ acyloxy, carboxy, $C_2$–$C_{12}$ alkoxycarbonyl, $C_6$–$C_{15}$ aryloxycarbonyl, amino, carbamoyl, and formyl.

Regioregular telechelic polymers can be synthesized with a cyclic olefin monomer of formula (VII) in which $X^{3A}$ is identical to $X^3$, $X^4$ is methylene or substituted methylene (i.e., $CR^{19}R^{20}$ wherein $R^{19}$ and $R^{20}$ are as defined earlier herein), $R^{18}$ is identical to $R^{17}$, and n is identical to m, such that the telechelic polymer resulting from the ROMP reaction is an unsaturated, regioregular polymer having the structure of formula (XII)

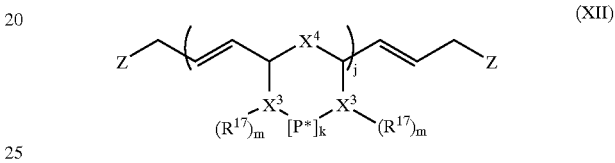

(XII)

wherein j is the number of recurring monomer units in the polymer, and $X^3$, $X^4$ $R^{17}$, k, and m are as defined with respect to formula (VIII). As above, when $X^3$ is O or S, such that k is 1 and m is zero, the telechelic polymer of formula (XII) has the structure of formula (XIIA)

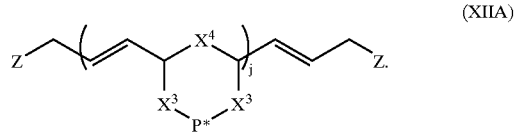

(XIIA)

Polymer (XII) may then be hydrogenated, as described previously, to give a saturated telechelic polymer having the structure (XIII)

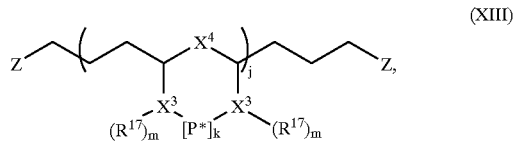

(XIII)

which, when $X^3$ is O or S, such that k is 1 and m is zero, has the structure of formula (XIIIA)

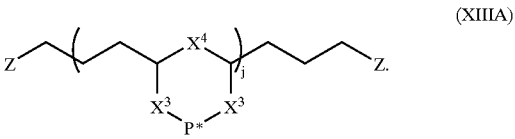

(XIIIA)

Deprotection of (XIII) provides a saturated, deprotected telechelic polymer having the structure of formula (XIV)

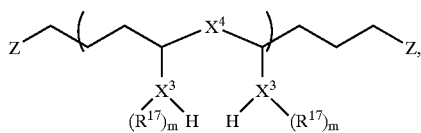

while deprotection of (XIIIA) results in a saturated, deprotected telechelic polymer having the structure of formula (XIVA)

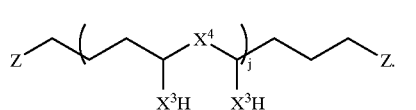

The regioregular polymers provided using the present methodology, including unsaturated, saturated, deprotected, and/or telechelic polymers, are novel polymers and are claimed as such herein. Accordingly, it will be appreciated in light of the above description that novel polymers of the invention include, but are not limited to, polymers of formulae (VIII), (VIIIA), (IX), (IXA), (X), (XA), (XII), (XIIA), (XIII), (XIIIA), (XIV), and (XIVA). Accordingly, the novel polymers can be generally represented as those comprised of recurring units having the structure of formula (XV)

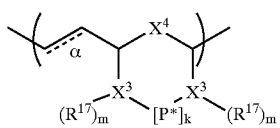

wherein:
α is an optional double bond;
$X^3$ is O, N or S;
$X^4$ is $CR^{19}R^{20}$ wherein $R^{19}$ and $R^{20}$ are independently selected from hydrogen, substituted hydrocarbyl, heteroatom-containing hydrocarbyl, substituted heteroatom-containing hydrocarbyl, and functional groups;
k is zero when $X^3$ is N, and k is 1 when $X^3$ is O or S;
m is zero when $X^3$ is O or S, and m is 1 when $X^3$ is N;
$R^{17}$ is selected from hydrogen, hydrocarbyl, substituted hydrocarbyl, heteroatom-containing hydrocarbyl, substituted heteroatom-containing hydrocarbyl, and amino-protecting groups, or the two $R^{17}$ substituents may be taken together to form a cyclic group; and
P* is a protecting group.

The polymer may be telechelic, in which case there are two terminal Z groups as indicated in formulae (XII) through (XIV), such that the polymer has the structure of formula (XVA)

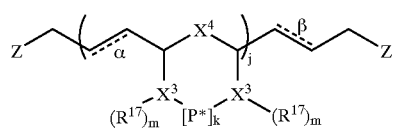

wherein j is the number of recurring monomer units in the polymer $X^3$, $X^4$ $R^{17}$, k, and m are as defined with respect to formula (VIII), and β is an optional double bond, wherein either both α and β are present as double bonds, or neither α nor β is present.

In another embodiment, the polymers are comprised of recurring units having the structure of formula (X)

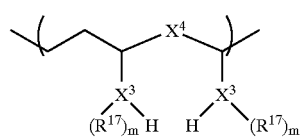

wherein $X^3$, $X^4$, $R^{17}$, and m are defined as for formula (XV), wherein, as above, the polymer may be telechelic and terminate in two Z groups, as described above with respect to polymers of formula (XVA).

Such polymers have the structure of formula (XB)

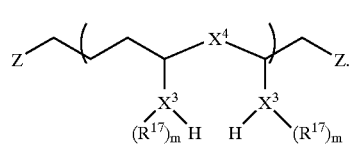

The novel polymers have a number average molecular weight in the range of approximately 1,000 to approximately 1,000,000. In the preferred novel polymers, $X^3$ is O or S, and $R^{19}$ and $R^{20}$ are hydrogen, such that the polymers are comprised of dyads having the structure of formula (XVI)

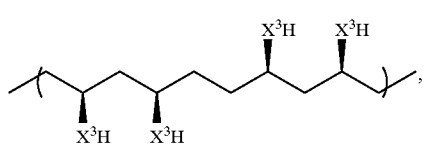

dyads having the structure of formula (XVII)

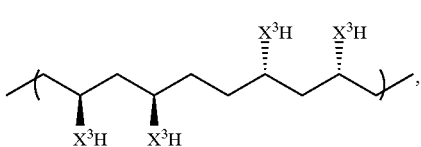

or combinations thereof, wherein $X^3$ is O or S. When $X^3$ is O and $T^1$ and $T^2$ are methyl, the polymer is regioregular MVOH, i.e., poly((vinyl alcohol)$_2$-alt-methylene).

Such polyolefins may be utilized in a further CMI reaction step to produce an alternating copolymer. Another embodiment of the invention provides a method for synthesizing an alternating copolymer via sequential olefin metathesis reactions in two steps, comprising:

(a) synthesizing a polyolefin intermediate using a ring-opening metathesis polymerization (ROMP) reaction by contacting a cyclic olefin monomer with a catalytically effective amount of an olefin metathesis catalyst under reaction conditions effective to allow the ROMP reaction to occur; and (b) contacting the polyolefin intermediate with a diene monomer having two terminal olefinic groups under reaction conditions effective to effect metathesis insertion of the diene monomer into the backbone of the polyolefin intermediate.

A preferred embodiment of the above invention is wherein the reaction conditions of (b) comprise carrying out the metathesis insertion reaction in the presence of a catalytically effective amount of the olefin metathesis catalyst of step (a).

Another preferred embodiment of the invention is such a process wherein the diene monomer is an acyclic diene and (b) comprises cross-metathesis insertion (CMI). The diene monomer having two terminal olefinic groups may be acyclic with respect to the terminal diene groups or may be generated in situ from a cyclic diene via a ring-opening cross metathesis (ROCM) reaction.

In another preferred embodiment of the invention, the cyclic olefin monomer is symmetric about an axis bisecting the olefinic functionality such that the polyolefin intermediate is regioregular. Still further preferred is such a process wherein the alternating copolymer that is produced is regioregular.

In one embodiment of the invention the polyolefin intermediate is not isolated between steps (a) and (b).

In another embodiment of the invention the polyolefin intermediate is isolated between steps (a) and (b) and purified.

In one preferred aspect the invention provides an alternating copolymer and a process for further modifying the copolymer. In such a process, a preferred method is wherein the further modification comprises removing protecting groups, hydrogenating olefinic bonds, hydrogenating carbonyl groups, substituting a second cyclic olefin residue into the alternating copolymer by a cross metathesis insertion to replace olefinic residues from the polyolefin intermediate, or combinations thereof.

In one embodiment the invention provides such a metathesis process wherein the catalysis is a Group 8 transition metal complex as described above. In a preferred process the metathesis catalyst is present in 0.0005 to 0.05 molar equivalents with respect to the cyclic olefin. Preferably, the diene is present in the reaction solution (such as an organic solvent) in a molar concentration from 0.2 to 2, more preferably 0.2 to 1, and most preferably from 0.2 to 0.5. Preferably, the cyclic olefin monomer is present in a molar ratio from 1:1 to 25:1 with respect to the cyclic olefin when the cyclic olefin is present in a ratio of 1.1:1 to 2:1 with respect to the diene.

Preferably the above process is carried out in an organic solvent. Further preferred is such a process carried out at reflux. Any solvent suitable for metathesis reactions may be utilized in the invention. Preferred organic solvents are dichloromethane, dichloroethane, toluene and the like.

Preferred dienes having two terminal olefinic groups that are useful in the methods according to the invention are dienes wherein are the two terminal olefinic groups of the diene are joined by a hydrocarbylene linker group comprising 6–30 carbon atoms and the carbon atoms of the linker group may be substituted or unsubstituted and the linker group may be interrupted by up to 6 hetero atoms selected from O, S and N, and on the linker chain two or more substituents may be linked to form an additional cyclic group. More preferred are such dienes wherein the two terminal olefinic groups of the diene taken together with adjacent atoms of the linker group form a bis-acrylate acyclic diene compound, a bis-vinyl ketone acyclic diene compound, or a bis-allylic acetate acyclic diene compound. Further preferred are such dienes wherein the linker group is hydrocarbylene, substituted hydrocarbylene, heteroatom-containing hydrocarbylene, or substituted heteroatom-containing hydrocarbylene linker, and two or more substituents on adjacent atoms of the chain may be linked to form an additional cyclic group, and wherein up to 6 carbon atoms of the linker group may be substituted by functional groups, or protected functional groups. Preferred functional groups or protected functional groups substituted on the carbon atoms of the linker group are independently selected from halogen, alcohol, oxo, thiol, —SO$_3$—H, a substituted —SO$_2$— group, amino, substituted amino, or combinations thereof.

A preferred acyclic diene useful in the present invention is selected from formula (VIIb) and (VIIc) as follows:

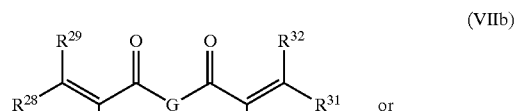

(VIIb)

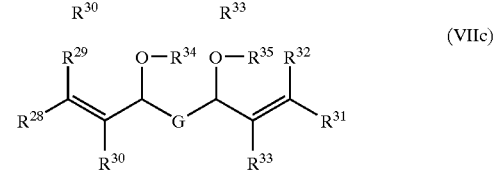

(VIIc)

wherein:

R$^{28}$, R$^{29}$, R$^{31}$, and R$^{32}$ are each independently hydrogen or a substituent that does not interfere with olefin cross metathesis;

R$^{30}$ and R$^{33}$ are each independently hydrogen or a leaving group that that does not interfere with olefin cross metathesis;

R$^{34}$ and R$^{35}$ are each independently hydrogen, a non-acyl alcohol protecting group, or an acyl group; and G is hydrocarbylene linker group comprising 6–30 carbon atoms, wherein the carbon atoms of the linker group may be substituted or unsubstituted and the linker group may be interrupted by up to 6 hetero atoms selected from O, S and N, and wherein two or more substituents on the chain may be linked to form an additional cyclic group.

Preferred dienes according to formulae (VIIb) and (VIIc) are such compounds wherein G is a linker chain constructed by 2 to 24 linked —X$^7$— groups, wherein each occurrence of X$^7$ in the linker chain is independently selected from CR$^{36}$R$^{37}$, O, S, or NR$^{38}$, and R$^{36}$, R$^{37}$, and R$^{38}$ are independently selected from hydrogen, substituted hydrocarbyl, heteroatom-containing hydrocarbyl, substituted heteroatom-containing hydrocarbyl, functional groups and protected functional groups, wherein up to 6 pairs of CR$^{36}$R$^{37}$ groups of the linker chain may be independently interrupted by an O, S, or NR$^{38}$ group.

A particularly preferred diene is a compound having one of the following structures:

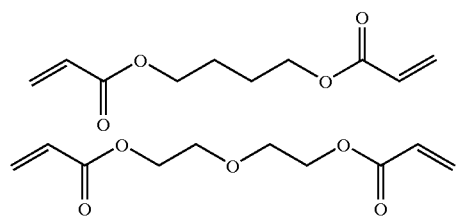

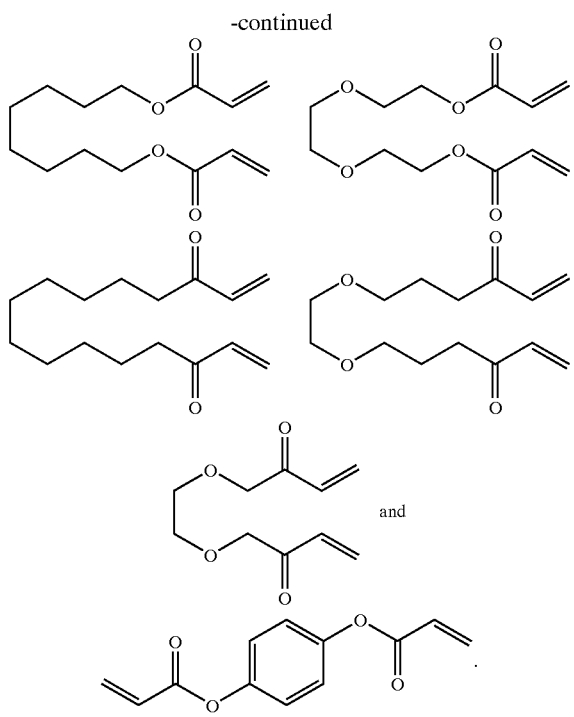

IV. Alternating Copolymers of the Invention

Reaction of the above cyclic olefins and dienes having two terminal olefinic groups produce alternating copolymers wherein the copolymer comprises a repeating unit selected from formula (VIId) and (VIIe) as follows:

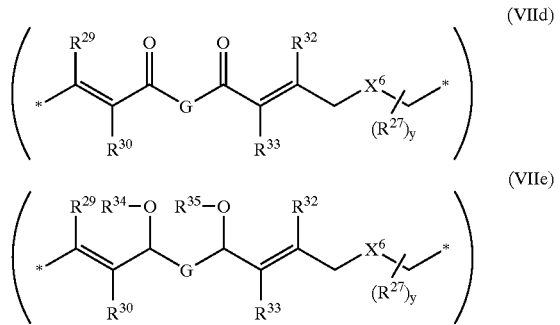

wherein:

$R^{28}$, $R^{29}$, $R^{31}$, and $R^{32}$ are each independently hydrogen or a substituent that does not interfere with olefin cross metathesis;

$R^{30}$ and $R^{33}$ are each independently hydrogen or a leaving group that that does not interfere with olefin cross metathesis;

$R^{34}$ and $R^{35}$ are each independently hydrogen, a non-acyl alcohol protecting group, or an acyl group;

G is hydrocarbylene linker group comprising 6–30 carbon atoms, wherein the carbon atoms of the linker group may be substituted or unsubstituted and the linker group may be interrupted by up to 6 hetero atoms selected from O, S and N, and wherein two or more substituents on the chain may be linked to form an additional cyclic group;

$X^6$ is a one-atom, two-atom, three-atom, four-atom or five atom linkage;

y is an integer from 0 to 4; and $R^{27}$ in each occurrence may replace a hydrogen atom on a ring carbon and each occurrence is independently selected from hydrocarbyl, substituted hydrocarbyl, heteroatom-containing hydrocarbyl, substituted heteroatom-containing hydrocarbyl, and -(L)$_v$-Fn wherein v is zero or 1, L is hydrocarbylene, substituted hydrocarbylene and/or heteroatom-containing hydrocarbylene, and Fn is a functional group, wherein two $R^{27}$ groups may collectively form a carbonyl group.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

EXPERIMENTAL

Alternating Copolymer via ROIMP Experimental

General Procedures. NMR spectra were recorded on Varian-300 NMR. Chemical shifts are reported in parts per million (ppm) downfield from tetramethylsilane (TMS) with reference to internal solvent. Multiplicities are abbreviated as follows: singlet (s), doublet (d), triplet (t), quartet (q), quintet (quint), and multiplet (m). The reported $^1$H NMR data refer to the major olefin isomer unless stated otherwise. The reported $^{13}$C NMR data include all peaks observed and no peak assignments were made. High-resolution mass spectra (EI and FAB) were provided by the UCLA Mass Spectrometry Facility (University of California, Los Angeles). Analytical thin-layer chromatography (TLC) was performed using silica gel 60 F254 precoated plates (0.25 mm thickness) with a fluorescent indicator. Flash column chromatography was performed using silica gel 60 (230–400 mesh) from EM Science. All other chemicals were purchased from the Aldrich, Strem, or Nova Biochem Chemical Companies, and used as delivered unless noted otherwise. CH$_2$Cl$_2$ was purified by passage through a solvent column prior to use. The solvent columns are composed of activated alumina (A-2) and supported copper redox catalyst (Q-5 reactant). See: A. B. Pangborn, M. A. Giardello, R. H. Grubbs, R. K. Rosen, F. J. Timmers, *Organometallics* 1996, 15, 1518–1520.

Materials. If necessary, non-anhydrous solvents were dried by passage through solvent purification columns. Cyclic olefins (>99%) were obtained from as described above unless otherwise stated and were used as received. Acyclic dienes were obtained from as described above and degassed by an argon purge prior to use. N,N-Dimethylformamide (anhydrous) (DMF), Toluene (anhydrous), dichloromethane (anhydrous), 1,2-dichloroethane (anhydrous), 2,6-lutidine (99+%, redistilled), and di-tert-butylsilylbis(trifluoromethanesulfonate) (97%) were obtained from Aldrich and used as received (after optionally being dried). (PCy$_3$)$_2$(Cl)$_2$Ru=CHPh (1) was synthesized according to Schwab et al. (1996) *J. Am. Chem. Soc.* 118: 100–110, (ImesH$_2$)—(PCy$_3$)(Cl)$_2$Ru=CHPh (2) was synthesized as described in Sanford et al. (2001) *J. Am. Chem. Soc.* 123:749–750, and 3,3-di-tert-butyl-2,4-dioxa-3-sila-bicyclo [3.2.1]oct-6-ene (3) was synthesized according to Lang et al. (1994) *Helv. Chim. Acta* 77:1527–1540.

Copolymerization of Cyclooctene and Butanediol Diacrylate via ROIMP with Catalyst (2)

A representative procedure for synthesis of a regioregular copolymer is shown in (Scheme 2), below.

SCHEME 2

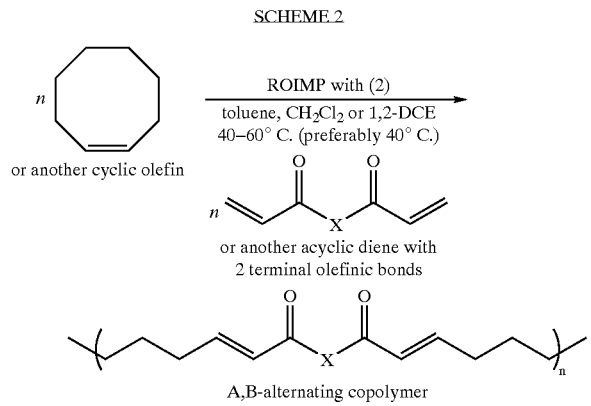

A,B-alternating copolymer

EXAMPLE 1

A small flask was charged with 1,4-butanediol diacrylate 90 mg, (0.45 mmol) in 2 mL of $CH_2Cl_2$ (solution of diene with two terminal olefinic groups) and a stir bar. Catalyst (2) 2.7 mg and cyclooctene 65 μL (0.45 mmol) (total monomer to catalyst ratio of 290:1 and monomer to monomer ratio of 1:1). The mixture was quickly degassed by dynamic vacuum and the flask was fitted with a condenser and heated at reflux under argon for 6 h. The product was precipitated into 50 mL of stirring methanol. The white polymer precipitate was washed several times with methanol and dried in vacuo overnight; yield of regioregular A,B-alternating copolymer product 108 mg (0.38 mmol), about 84% yield. The polymer had a high molecular weight of 90100 g $mol^{-1}$ (Mn/PDI, determined by $CH_2Cl_2$ GPC relative to polystyrene standards). $^1H$ NMR (300 MHz, $CDCl_3$): δ=6.93 (dt, J=7.2, 15.9 Hz, 1H), 577 (d,J=15.9 Hz, 1H), 4.13 (br s, 2H), 2.12 (m, 2H), 1.73 (m, 2H), 1.43 (m, 2H), 1.30 ppm (m, 2H). $^{13}C$ NMR (75 MHz, $CDCl_3$): δ=166.8, 149.6, 121.3, 64.0, 32.5, 29.3, 28.2, 25.8 ppm. (See FIG. 1 NMR).

The above example represents the treatment of a 1:1 mixture of monomers A (diacrylates) and B (cycloalkenes) with catalyst (2), indeed, yielding highly A,B-alternating copolymers in high yields. For example, with a total monomer/catalyst ratio of just 290:1, a 1:1 mixture of 1,4-butanediol diacrylate and cyclooctene gave an 84% yield of a copolymer with up to 99% A,B-alternation and a molecular weight of 90100 $cmol^{-1}$. It is important to match the stoichiometry of cyclooctene because any excess of cyclooctene results in oligocyclooctene blocks, which lowers the A,B-alternation. The extent of A,B-alternation could be easily determined by $^1H$ NMR spectroscopic analysis, since olefinic protons for A,B-alternating units have a distinct chemical shift from the starting materials and homo-coupled units. E-Acrylate dimmers produce a sharp singlet at δ=6.9 ppm (FIG. 1, entry a), whereas polycycloalkenes display a multiplet at δ=5.4 ppm (FIG. 1, entry c). On the other hand, A,B-alternating units produce a doublet of triplets at δ=7.0 ppm and a doublet at δ=5.8 ppm (FIG. 1 entry b). Therefore, the extent of A,B-alternation can be easily calculated by integrating these peaks. The sharp coupling patterns demonstrate a highly uniform polymer structure with E olefin isomer (J=15.9 Hz). $^{15}C$NMR spectroscopic analysis also shows high A,B-alternation, displaying only two olefinic carbon peaks for carbon atoms α and β to the carbonyl group (FIG. 1, entry d).

EXAMPLE 1A

Example 1 was repeated except that the cyclic olefin (cyclooctene) was replaced with the bicyclic olefin norborene and the reaction was conducted with a monomer/catalyst ratio of 100. The white polymer precipitate was washed several times with methanol and dried in vacuo overnight to provide a yield of 95% regioregular A,B-alternating copolymer product in about 87% yield.

EXAMPLE 1B

Example 1 was repeated except that the diene (1,4-butanediol diacrylate) was replaced with the a diene having the formula $CH_2$=CH—C(=O)—N(-phenyl)-$(CH_2)_6$—N(-phenyl)-C(=O)—CH=$CH_2$ and the reaction was conducted with at a catalyst concentration of 3.3 mole percent with respect to the diene. The polymer precipitate was washed several times with methanol and dried in vacuo overnight to provide a yield of 95% regioregular A,B-alternating copolymer product in about 99% yield, having a MW of 9700 and a PDI of 1.45.

EXAMPLES 2–7

Copolymerization of Cycloalkenes and Acyclic Dienes via ROIMP with Catalyst (2)

EXAMPLE 2

To a flask charged with 1,4-butanediol diacrylate (34 mg, 0.15 mmol) in 0.4 ml of $CH_2Cl_2$, catalyst 2 (2.3 mg) and cyclopentene (20 μl, 0.15 mmol) were added. Quick degassing by dynamic vacuum was conducted and the flask was fitted with a condenser and refluxed under argon for 6 hours. The product (37 mg, 75%) was precipitated into hexane. $^1H$ NMR (300 MHz, $CDCl_3$, ppm): δ 6.85 (1H, dt, J=7.2, 15.9 Hz), 5.82 (1H, d, J=15.9 Hz), 4.10 (2H, broad), 2.22 (2H, m), 1.60–1.75 (3H, m). $^{13}C$ NMR (75 MHz, $CDCl_3$, ppm), δ 166.5, 148.4, 121.9, 64.0, 31.7, 30.7, 26.6, 25.6.

EXAMPLE 3

To a flask charged with 1,4-butanediol diacrylate (60 mg, 0.30 mmol) in 0.8 ml of $CH_2Cl_2$, catalyst 2 (4.1 mg) and cycloheptene (35.5 μl, 0.30 mmol) were added. Quick degassing by dynamic vacuum was conducted and the flask was fitted with a condenser and refluxed under argon for 6 hours. The product (74 mg, 93%) was precipitated into hexane. $^1H$ NMR (300 MHz, $CDCl_3$, ppm): δ 6.93 (1H, dt, J=6.9, 15.3 Hz), 5.78 (1H, dt, J=1.5, 7.0 Hz), 4.13 (2H, broad), 2.17 (2H, m), 1.72 (2H, m), 1.30–1.42 (3H, m). $^{13}C$ NMR (75 MHz, $CDCl_3$, ppm), δ 166.8, 149.5, 121.4, 64.0, 32.4, 29.0, 28.1, 25.8.

EXAMPLE 4

To a flask charged with 1,4-butanediol diacrylate (60 mg, 0.30 mmol) in 0.6 ml of $CH_2Cl_2$, catalyst 2 (2.6 mg) and cyclododecene (58 μml, 0.30 mmol) were added. Quick degassing by dynamic vacuum was conducted and the flask was fitted with a condenser and refluxed under argon for 6 hours. The product (92 mg, 91%) was precipitated into methanol. $^1H$ NMR (300 MHz, $CDCl_3$, ppm): δ 6.94 (1H, dt, J=7.2, 15.3 Hz), 5.80 (1H, dt, J=1.5, 15.9 Hz), 4.13 (2H, t, J=5.1 Hz), 2.16 (2H, dt, J=6.9, 6.6 Hz), 1.73 (2H, t, J=3.0 Hz), 1.42 (2H, m), 1.24 (7H, m). $^{13}C$ NMR (75 MHz, $CDCl_3$, ppm), δ 166.9, 149.9, 121.2, 64.0, 32.6, 29.9, 29.8, 29.5, 28.4, 25.8.

EXAMPLE 5

To a flask charged with 1,4-butanediol diacrylate (40 mg, 0.20 mmol) in 0.5 ml of $CH_2Cl_2$, catalyst 2 (1.4 mg) and cyclododecene (54 mg, 0.20 mmol) were added. Quick degassing by dynamic vacuum was conducted and the flask was fitted with a condenser and refluxed under argon for 6 hours. The product (60 mg, 69%) was precipitated into methanol. $^1$H NMR (300 MHz, $CDCl_3$, ppm): δ 6.96 (1H, dt, J=6.6, 16.2 Hz), 5.80 (1H, d, J=15.9 Hz), 4.16 (2H, broad), 3.69 (1H, m), 2.20 (2H, m), 1.75 (2H, broad), 1.58 (1H, m) 1.46 (2H, m), 0.90(9H, s), 0.03(6H, s). $^{13}$C NMR (75 MHz, $CDCl_3$, ppm), δ 166.7, 149.6, 149.3, 121.5, 121.2, 71.4, 64.0, 36.7, 35.5, 21.7, 28.3, 26.2, 25.8, 24.0, 18.4, −3.9, −4.0.

EXAMPLE 6

To a flask charged with tri(ethylene glycol) diacrylate (53 mg, 0.21 mmol) in 1 ml of $CH_2Cl_2$, catalyst 2 (1.8 mg) and cyclooctene (28 μl, 0.21 mmol) were added. Quick degassing by dynamic vacuum was conducted and the flask was fitted with a condenser and refluxed under argon for 6 hours. The product (68 mg, 99%) was precipitated into hexane. $^1$H NMR (300 MHz, $CDCl_3$, ppm): δ 6.95 (1H, dt, J=6.9, 15.9 Hz), 5.82 (1H, d, J=15.9 Hz), 4.26 (2H, t, J=4.8 Hz), 3.70 (2H, t, J=5.1 Hz), 3.64 (2H, s), 2.16 (2H, dt, J=6.6, 6.6 Hz), 1.42 (2H, m) 1.29 (2H, m). $^{13}$C NMR (75 MHz, $CDCl_3$, ppm), δ 166.7, 150.0, 121.2, 70.8, 69.6, 63.6, 32.5, 29.3, 28.2.

EXAMPLE 7

To a flask charged with hydroquinone diacrylate (44 mg, 0.21 mmol) in 1 ml of $CH_2Cl_2$, catalyst 2 (3.5 mg) and cyclooctene (27.5 μl, 0.21 mmol) were added. Quick degassing by dynamic vacuum was conducted and the flask was fitted with a condenser and refluxed under argon for 6 hours. The product (60 mg, 98%) was precipitated by hexane. $^1$H NMR (300 MHz, $CDCl_3$, ppm): δ 7.11–7.20 (3H, m), 6.00 (1H, d, J=15.3 Hz), 2.27 (2H, dt, J=6.9, 6.3 Hz), 1.52 (2H, broad), 1.37 (2H, broad). $^{13}$C NMR (75 MHz, $CDCl_3$, ppm), δ 165.0, 152.0, 148.2, 122.6, 120.7, 32.7, 29.3, 28.2.

As illustrated by Examples 2–7, above, cycloalkenes other than cyclooctene of Example 1, were also viable for ROIMP (e.g., cyclopentene, cycloheptene, and cyclododecene) and yielded highly A,B-alternating polymers in Examples 2–7, above. However, substrates with particularly low ring strain, such as cyclopentene and cycloheptene, required a lower monomer/catalyst ratio (125:1) as a result of the slow rate of ROMP.[9] To obtain a high A,B-alternation (96%) with volatile cyclopentene (b.p. 44° C.), a slight excess (1.3 equiv) of the cycloalkene relative to the diacrylate was used. Even with 2.0 equivalents of cyclopentene, a polymer with higher than 85% A,B-alternation with catalyst 3 yielded a final polymer with higher A,B-alternation. These results suggest that the equilibrium for cyclopentene lies toward the cyclic form at 40° C.; excess homopolycyclopentene units are degraded back to cyclopentene and lost from the system by evaporation.

Notably, various functional groups can be incorporated into ROIMP copolymers. 5-tert-Butyldimetheylsilyoxycyclooctene proved to be a viable monomer, comparable to the parent cyclooctene. In this way, free alcohol groups could be installed into alternating monomer units upon simple deprotection. Further variations such as ethylene glycol and phenyl groups can be substituted into diacrylate units. Results with such protected and substituted reactants have demonstrated that the regioselective incorporation of functional groups is possible by the appropriate choice of monomers A and B, thus opening up a new class of polymers that can be synthesized by ROIMP. Accordingly, the process shown in Scheme 2, and described in detail above, was repeated using various cyclic olefins and acyclic dienes having two terminal olefinic groups at varying ratios of reactants and catalyst (2) at 40° C. (Table 1, below). All of the copolymerizations reached high regioregularity (≧94%) in high yield (69%–99%) and were fully characterized by $^1$H/$^{13}$C NMR. Over the molecular weight range $1.4 \times 10^4$ to $9.0 \times 10^4$ g/mol, PDI values were relatively low (See Table 1, below).

TABLE 1

| Entry | Diacrylate | Cycloalkene[a] | M/C[b] | Conc. [M][c] | Yield [%][d] | A,B-alt. [%][e] | Mn/PDI [×10$^{-3}$ g mol$^{-1}$][f] |
|---|---|---|---|---|---|---|---|
| 1 | (acrylate structure) | (cyclooctene) | 290 | 0.2 | 84 | 99 | 90.0/1.73 |
| 1A | (acrylate structure) | (norbornene) | 100 | — | 87 | 95 | — |

TABLE 1-continued

| Entry | Diacrylate | Cycloalkene[a] | M/C[b] | Conc. [M][c] | Yield [%][d] | A,B-alt. [%][e] | Mn/PDI [×10$^{-3}$ g mol$^{-1}$][f] |
|---|---|---|---|---|---|---|---|
| 1B | 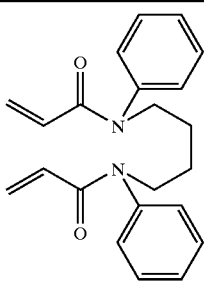 | 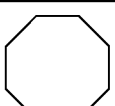 | — | 0.3 | 99 | 97 | 9.7/1.45 |
| 2 | same |  | 125 | 0.4 | 75 | 96 | 20.3/1.58 |
| 3 | same | 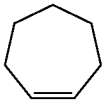 | 125 | 0.4 | 93 | 97 | 14.0/1.80 |
| 4 | same | 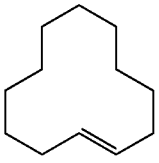 | 200 | 0.5 | 91 | 94 | 26.1/1.71 |
| 5 | same | 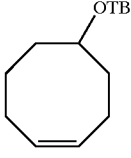 | 250 | 0.4 | 69 | 94.5 | 21.4/1.43 |
| 6 | 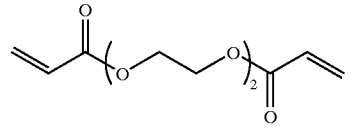 | 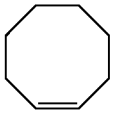 | 200 | 0.2 | 99 | 98.5 | 26.5/1.80 |
| 7 | 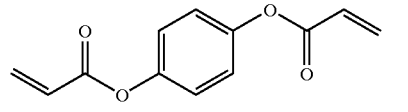 | 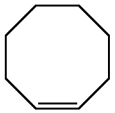 | 100 | 0.1 | 98 | 97 | 25.2/2.06 |

[a]1.0 Equivalents of cycloalkene was used, except for cyclopentene (1.3 equiv).
[b]Total monomer/catalyst ratio.
[c]Concentration with respect to diacrylate.
[d]Yields of isolated products after precipitation into hexane or methanol.
[e]Determined by $^1$H NMR spectroscopic analysis.
[f]Determined by $CH_2Cl_2$ GPC relative to polystyrene standards.

ROIMP exhibits remarkable conversion and selectivity. Compared to ADMET, where high vacuum and elevated temperatures are required to drive the polymerization to high conversion by removal of ethylene gas, ROIMP gives high conversion under gentle reflux conditions for two reasons. First, ROMP of the cyclic olefin (monomer B) is efficient in making the initial homopolycycloalkene chains. Second, the formation of 1,2-disubstituted α,β-unsaturated carbonyl compounds is thermodynamically favored by more than 3 kcal mol$^{-1}$ per bond. These enthalpic factors, combined with the loss of ethylene, drive the reaction to high conversion. Furthermore, the unfavorable oligomerization of diacrylates, in which the intermediate is an unstable enoic carbene, leads to high A,B-alternation. Therefore, ROIMP has benefits of both chain-growth and step-growth polymerization, leading to high molecular weight and high selectivity.

To optimize conversion, other polymerization conditions were investigated. It was found that 0.1–0.5 M solutions in $CH_2Cl_2$ at 40° C. give the best results. In contrast to ROMP, increasing the concentration beyond 0.5 M resulted in lower conversion. Switching to toluene or 1,2-dichloroethane as the solvent also gave lower conversion at either 40° C. or 60° C. Although $CH_2Cl_2$ has sometimes been shown to be the best solvent for cross metathesis of functionalized olefins, the concentration dependence for ROIMP is somewhat surprising, since concentrations of 0.1–0.5 M are considered dilute conditions for conventional step-growth-polymerization reactions.

Controlling the molecular weight of polymers is a very important issue since polymers with different molecular weights often exhibit different properties. For alternating copolymers produced by ROIMP, molecular weight can be roughly controlled by changing the relative stoichiometry of the two monomers. For example, using 0.96 equivalents of cyclooctene to 1.0 equivalent of hydroquinone diacrylate gave a copolymer of 17800 g mol$^{-1}$ with 98% A,B-alternation (PDI=1.64), whereas a copolymer of 45200 g mol$^{-1}$ and 95.5% A,B-alternation (PDI=1.69) was obtained by increasing the cyclooctene to 1.06 equivalents. These results show that when compared with the 1:1 case (Table 1, entry 7 above), an excess of hydroquinone diacrylate shortens the polymer chain, but an excess of cyclooctene gives higher molecular weight as a result of the oligomeric blocks of polycyclooctene.

In conclusion, the above experimental results demonstrate a new general method for synthesizing highly alternating copolymers by olefin metathesis. The high conversion and degree of alternation appear to arise in part from the thermodynamically driven selective bond formation between diacrylates and cycloalkenes.

We claim:

1. A method for synthesizing a copolymer via an olefin metathesis insertion reaction, comprising contacting a polyolefin with a diene monomer having two terminal olefinic groups in the presence of a catalytically effective amount of an olefin metathesis catalyst under reaction conditions effective to provide metathesis insertion of the diene monomer into the backbone of the polyolefin, wherein the concentration of the diene in the reaction medium is from 0.2 to 2 molar.

2. The method of claim 1 wherein the polyolefin is regioregular and the copolymer is a regioregular alternating copolymer.

3. A method for synthesizing an alternating copolymer via sequential olefin metathesis reactions, comprising:
   (a) synthesizing a polyolefin intermediate using a ring-opening metathesis polymerization (ROMP) reaction by contacting a cyclic olefin monomer with a catalytically effective amount of an olefin metathesis catalyst under reaction conditions effective to allow the ROMP reaction to occur; and
   (b) contacting the polyolefin intermediate with a diene monomer having two terminal olefinic groups under reaction conditions effective to effect metathesis insertion of the diene monomer into the backbone of the polyolefin intermediate.

4. The method of claim 3, wherein the reaction conditions of (b) comprise carrying out the metathesis insertion reaction in the presence of a catalytically effective amount of the olefin metathesis catalyst of step (a).

5. The method of claim 3, wherein the diene monomer is an acyclic diene and (b) comprises cross-metathesis insertion (CMI).

6. The method of claim 3, wherein the diene monomer having two terminal olefinic groups is generated in situ from a cyclic diene via a ring-opening cross metathesis (ROCM) reaction.

7. The method of claim 3, wherein the cyclic olefin monomer is symmetric about an axis bisecting the olefinic functionality such that the polyolefin intermediate is regioregular.

8. The method of claim 7, wherein the alternating copolymer is regioregular.

9. The method of claim 3, wherein the polyolefin intermediate is not isolated between steps (a) and (b).

10. The method of claim 3 wherein following (b), the alternating copolymer is isolated and purified.

11. The method of claim 3, wherein following (b), the alternating copolymer is further modified.

12. The method of claim 11, wherein the further modification comprises removing protecting groups, hydrogenating olefinic bonds, hydrogenating carbonyl groups, substituting a second cyclic olefin residue into the alternating copolymer by a cross metathesis insertion to replace olefinic residues from the polyolefin intermediate, or combinations thereof.

13. The method of claim 3, wherein the olefin metathesis catalyst is a Group 8 transition metal complex having the structure of formula (I)

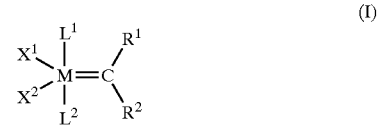

in which

M is a Group 8 transition metal;

$L^1$ and $L^2$ are neutral electron donor ligands;

$X^1$ and $X^2$ are anionic ligands; and $R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $R^1$, and $R^2$ can be taken together to form a cyclic group, and further wherein any one of $X^1$, $X^2$, $L^1$, $L^2$, $R^1$, and $R^2$ can be attached to a support.

14. The method of claim 13, wherein:

$R^1$ is hydrogen, and $R^2$ is selected from $C_1$–$C_{20}$ alkyl, $C_2$–$C_{20}$ alkenyl, and $C_5$–$C_{20}$ aryl, optionally substituted with one or more moieties selected from $C_1$–$C_6$ alkyl, $C_1$–$C_6$ alkoxy, and phenyl;

$L^1$ and $L^2$ are independently selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether; and $X^1$ and $X^2$ are independently selected from hydrogen, halide, $C_1$–$C_{20}$ alkyl, $C_5$–$C_{20}$ aryl, $C_1$–$C_{20}$ alkoxy, $C_5$–$C_{20}$ aryloxy, $C_2$–$C_{20}$ alkoxycarbonyl, $C_6$–$C_{20}$ aryloxycarbonyl, $C_2$–$C_{20}$ acyl, $C_2$–$C_{20}$ acyloxy, $C_1$–$C_{20}$ alkylsulfonato, $C_5$–$C_{20}$ arylsulfonato, $C_1$–$C_{20}$ alkylsulfanyl, $C_5$–$C_{20}$ arylsulfanyl, $C_1$–$C_{20}$ alkylsulfinyl, or $C_5$–$C_{20}$ arylsulfinyl, any of which, with the exception of hydrogen and halide, are optionally further substituted with one or more groups selected from halide, $C_1$–$C_6$alkyl, $C_1$–$C_6$alkoxy, and phenyl.

15. The method of claim 14, wherein:

$R^2$ is selected from phenyl, vinyl, methyl, isopropyl, and t-butyl;

$L^1$ and $L^2$ are phosphines of the formula $PR^5R^6R^7$, where $R^5$, $R^6$, and $R^7$ are each independently aryl or $C_1$–$C_{10}$ alkyl; and $X^1$ and $X^2$ are independently selected from halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate.

16. The method of claim 15, wherein:
$R^2$ is phenyl or vinyl;
$L^1$ and $L^2$ are selected from tricyclohexylphosphine, tricyclopentylphosphine, triisopropylphosphine, triphenylphosphine, diphenylmethylphosphine, and phenyldimethylphosphine; and
$X^1$ and $X^2$ are halide.

17. The method of claim 16, wherein:
$R^2$ is phenyl;
$L^1$ and $L^2$ are the same, and are selected from tricyclohexylphosphine and tricyclopentyiphosphine; and
$X^1$ and $X^2$ are chloro.

18. The method of claim 3, wherein the process is carried out in an organic solvent.

19. The method of claim 18, wherein the process is carried out at reflux.

20. The method of claim 3, wherein the metathesis catalyst is present in 0.0005 to 0.05 molar equivalents with respect to the cyclic olefin.

21. The method of claim 18, wherein the diene is present in a molar concentration from 0.2 to 2 in the organic solvent.

22. The method of claim 21, wherein the cyclic olefin monomer is present in a molar ratio from 1:1 to 25:1 with respect to the diene.

23. The method of claim 22, wherein the metathesis catalyst is present at about 0.05 percent with respect to the molar concentration of the cyclic olefin.

24. The method of claim 3, wherein the cyclic olefin monomer is present in a molar ratio from 1:1 to 25:1 with respect to the diene.

25. The method of claim 24, wherein the cyclic olefin monomer is present in a molar ratio from 1:1 to 2:1 with respect to the diene.

26. The method of claim 25, wherein the cyclic olefin monomer is present in a molar ratio of about 1.1:1 with respect to the diene.

27. The method of claim 3, wherein the cyclic olefin monomer has the structure of formula (IV)

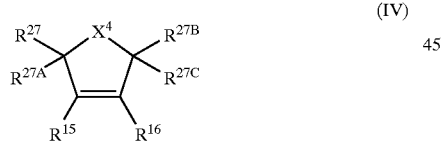

(IV)

wherein:
$X^4$ is a one-atom to five-atom linkage;
one of $R^{15}$ and $R^{16}$ is hydrogen and the other is selected from hydrocarbyl, substituted hydrocarbyl, heteroatom-containing hydrocarbyl, and substituted heteroatom-containing hydrocarbyl, and $-(L)_v$-Fn wherein v is zero or 1, L is hydrocarbylene, substituted hydrocarbylene and/or heteroatom-containing hydrocarbylene, and Fn is a protected or unprotected functional group; and
$R^{27}$, $R^{27A}$, $R^{27B}$, and $R^{27C}$ are independently selected from hydrogen, hydrocarbyl, substituted hydrocarbyl, heteroatom-containing hydrocarbyl, substituted heteroatom-containing hydrocarbyl, and $-(L)_v$-Fn, and further wherein any two of $R^{27}$, $R^{27A}$, $R^{27B}$, and $R^{27C}$ may be taken together to form a cyclic structure, such that the olefin monomer is bicyclic, with the proviso that when the olefin monomer is bicyclic, then $X^4$ is a one-atom or two-atom linkage.

28. The method of claim 27, wherein $R^{15}$ and $R^{16}$ are hydrogen.

29. The method of claim 28, wherein $X^4$ has the formula $-R^{19}CR^{20}-(X^5)_h-$ wherein h is zero or 1, $X^5$ is $CR^{21}R^{22}$, O, S, or $NR^{23}$, and $R^{19}$, $R^{20}$, $R^{21}$, $R^{22}$, and $R^{23}$ are independently selected from hydrogen, substituted hydrocarbyl, heteroatom-containing hydrocarbyl, substituted heteroatom-containing hydrocarbyl, functional groups, protected functional groups, and $R^{20}$ and $R^{21}$ taken together may form a carbonyl group.

30. The method of claim 29, wherein h is zero.

31. The method of claim 30, wherein $R^{19}$ and $R^{20}$ are hydrogen.

32. The method of claim 27, wherein $R^{27A}$ and $R^{27C}$ are hydrogen, $R^{27}$ is $-(L)_v$-Fn wherein v is zero and -Fn is $-X^{3A}-(R^{18})_n$, and $R^{27B}$ is $-(L)_v$-Fn wherein v is zero and -Fn is $-X^3-(R^{17})_m$, and further wherein $X^3$ and $X^{3A}$ are directly or indirectly lin the cyclic olefin monomer has the structure of formula (VII)

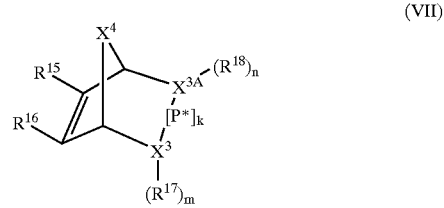

(VII)

in which:
$X^4$ is a one-atom or two-atom linkage;
$R^{15}$ and $R^{16}$ are as defined previously;
$X^3$ and $X^{3A}$ are independently N, O, or S;
k is zero or 1;
m and n are independently zero or 1;
P* is a heteroatom-protecting group;
$R^{17}$ and $R^{18}$ are independently selected from hydrogen, hydrocarbyl, substituted hydrocarbyl, heteroatom-containing hydrocarbyl, substituted heteroatom-containing hydrocarbyl, and amino protecting groups, wherein $R^{17}$ and $R^{18}$ may be taken together to form a cyclic group, with the provisos that:
when $X^3$ is O or S, then m is zero;
when $X^{3A}$ is O or S, then n is zero;
when $X^3$ is N, then m is 1; and
when $X^{3A}$ is N, then n is 1.

33. The method of claim 27, wherein $R^{27A}$ and $R^{27C}$ are hydrogen, such that the cyclic olefin has the structure of formula (VIIA)

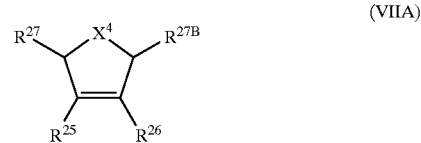

(VIIA)

wherein $X^4$, $R^{27}$, and $R^{27B}$ are as defined previously, and $R^{25}$ and $R^{26}$ are defined as for $R^{15}$ and $R^{16}$.

34. The method of claim 33, wherein $X^4$ is $C_1$ to $C_5$ alkylene or substituted $C_1$ to $C_5$ alkylene.

35. The method of claim 34, wherein the substituted $C_1$ to $C_5$ alkylene is substituted by at least one alcohol or protected alcohol group.

36. The method of claim 38, wherein an alcohol group is protected by a TBS group, an acyl group, or a tetrahydropyran group.

37. The method of claim 3, wherein the cyclic olefin monomer is selected from cyclopentene, 3-methylcyclopentene, 4-methylcyclopentene, 3-t-butyldimethylsilyloxy-cyclopentene, 4-t-butyldimethylsilyloxycyclopentene, cyclohexene, 3-methylcyclohexene, 4-methyl-cyclohexene, 3-t-butyldimethylsilyloxycyclohexene, 4-t-butyldimethylsilyloxy-cyclohexene, cycloheptene, 3-methylcycloheptene, 4-methylcycloheptene, 5-methylcycloheptene, 3-t-butyldimethylsilyloxy-cycloheptene, 4-t-butyldimethylsilyloxycycloheptene, 5-t-butyldimethylsilyloxycycloheptene, cyclooctene, 3-methylcyclooctene, 4-methylcyclooctene, 5-methylcyclooctene, 3-t-butyldimethylsilyloxycyclooctene, 4-t-butyldimethylsilyloxycyclopentene, 5-t-butyldimethylsilyloxycyclooctene, cyclononene, 3-methylcyclononene, 4-methylcyclononene, 5-methylcyclononene, 6-methylcyclo-nonene, 3-t-butyldimethylsilyloxycyclononene, 4-t-butyl dimethylsilyloxycyclononene, 5-t-butyl dimethylsilyloxycyclononene, 6-t-butyl dimethylsilyloxycyclononene, cyclodecene, 3-methylcycloundecene, 4-methylcyclodecene, 5-methylcyclodecene, 6-methylcyclodecene, 3-t-butyldimethylsilyloxy-oxycyclodecene, 4-t-butyl dimethylsilyloxycyclononene, 5-t-butyldimethylsilyloxycyclodecene, 6-t-butyldimethylsilyloxycyclodecene, cycloundecene, 3-methylcycloundecene, 4-methylcycloundecene, 5-methylcycloundecene, 6-methylcycloundecene, 7-methylcycloundecene, 3-t-butyldimethylsilyloxycycloundecene, 4-t-butyldimethylsilyloxycycloundecene, 5-t-butyldimethylsilyloxycycloundecene, 6-t-butyldimethylsilyloxycycloundecene, 7-t-butyldimethylsilyloxycycloundecene, cyclododecene, 3-methylcyclododecene, 4-methylcyclododecene, 5-methylcyclododecene, 6methyl-cyclododecene, 7-methylcyclo-dodecene, 3-t-butyldimethylsilyloxycyclododecene, 4-t-butyldimethylsilyloxycyclododecene, 5-t-butyldimethylsilyloxycyclododecene, 6-t-butyldimethylsilyloxycyclododecene, and 7-t-butyldimethylsilyloxycyclododecene.

38. The method of claim 37, wherein the cyclic olefin monomer is selected from cyclopentene, 3-methylcyclopentene, 3-t-butyldimethylsilyloxycyclopentene, cyclohexene, 4-methylcyclohexene, 4-t-butyldimethylsilyloxycyclohexene, cycloheptene, cyclooctene, 5-methylcyclo-octene, 5-t-butyldimethylsilyloxycyclooctene, cyclononene, and cyclododecene.

39. The method of claim 3, wherein the two terminal olefinic groups of the diene are joined by a hydrocarbylene linker group comprising 6–30 carbon atoms, wherein the carbon atoms of the linker group may be substituted or unsubstituted and the linker group may be interrupted by up to 6 hetero atoms selected from O, S and N, and wherein two or more substituents on the chain may be linked to form an additional cyclic group.

40. The method of claim 39, wherein the two terminal olefinic groups of the diene taken together with adjacent atoms of the linker group form a bis-acrylate acyclic diene compound, a bis-vinyl ketone acyclic diene compound, or a bis-allylic acetate acyclic diene compound.

41. The method of claim 40, wherein the linker group is hydrocarbylene, substituted hydrocarbylene, heteroatom-containing hydrocarbylene, or substituted heteroatom-containing hydrocarbylene linker, and two or more substituents on adjacent atoms of the chain may be linked to form an additional cyclic group, and wherein up to 6 carbon atoms of the linker group may be substituted by functional groups, or protected functional groups.

42. The method of claim 41, wherein functional groups or protected functional groups substituted on the carbon atoms of the linker group are independently selected from halogen, alcohol, oxo, thiol, —SO$_3$—H, a substituted —SO$_2$— group, amino, substituted amino, or combinations thereof.

43. The method of claim 40, wherein the acyclic diene is a selected from formula (VIIb) and (VIIc) as follows:

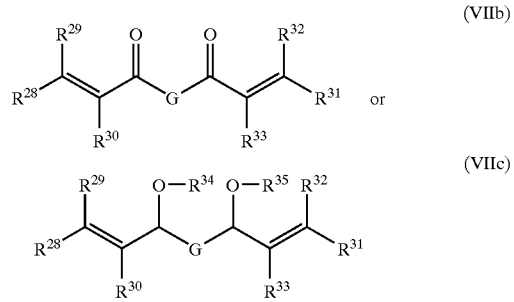

wherein:

$R^{28}$, $R^{29}$, $R^{31}$, and $R^{32}$ are each independently hydrogen or a substituent that does not interfere with olefin cross metathesis, $R^{30}$ and $R^{33}$ are each independently hydrogen or a leaving group that that does not interfere with olefin cross metathesis, $R^{34}$ and $R^{35}$ are each independently hydrogen, a non-acyl alcohol protecting group, or an acyl group, and G is hydrocarbylene linker group comprising 6–30 carbon atoms, wherein the carbon atoms of the linker group may be substituted or unsubstituted and the linker group may be interrupted by up to 6 hetero atoms selected from O, S and N, and wherein two or more substituents on the chain may be linked to form an additional cyclic group.

44. The method of claim 43, wherein G is a linker chain constructed by 2 to 24 linked —X$^7$— groups, wherein each occurrence of X$^7$ in the linker chain is independently selected from CR$^{36}$R$^{37}$, O, S or NR$^{38}$, and R$^{36}$, R$^{37}$, and R$^{38}$ are independently selected from hydrogen, substituted hydrocarbyl, heteroatom-containing hydrocarbyl, substituted heteroatom-containing hydrocarbyl, functional groups and protected functional groups, wherein up to 6 pairs of CR$^{36}$R$^{37}$ groups of the linker chain may be independently interrupted by an O, S, or NR$^{38}$ group.

45. The method of claim 44, wherein the acyclic diene has a structure selected from the following formulae:

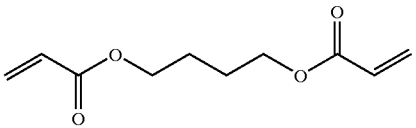

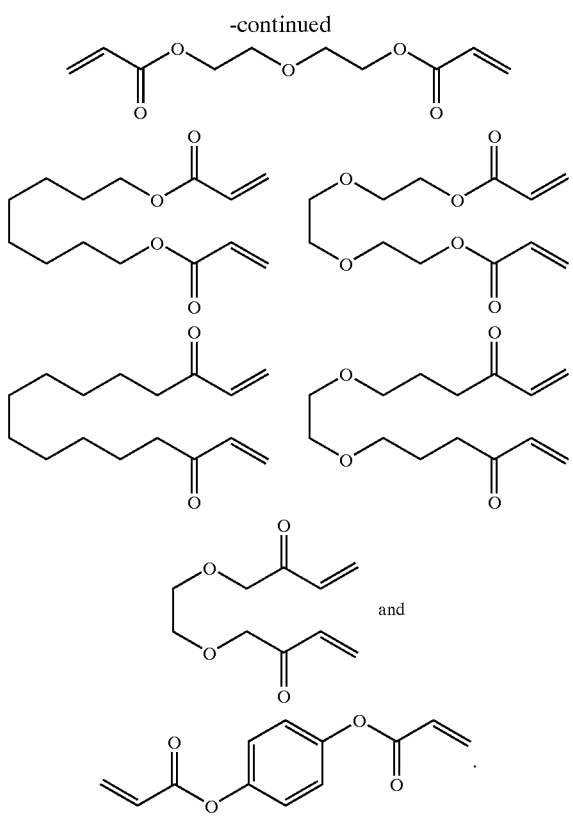

and

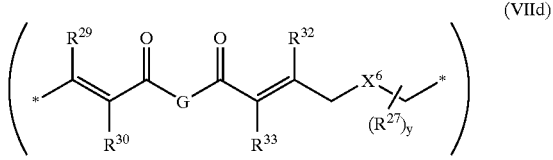

46. The method of claim 3, wherein the copolymer is a copolymer comprising a repeating unit selected from formula (VIId) and (VIIe) as follows:

(VIId)

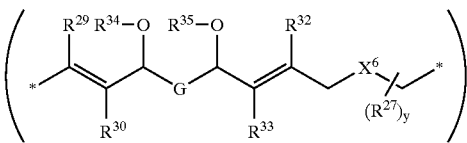

(VIIe)

wherein:

$R^{28}$, $R^{29}$, $R^{31}$, and $R^{32}$ are each independently hydrogen or a substituent that does not interfere with olefin cross metathesis, $R^{30}$ and $R^{33}$ are each independently hydrogen or a leaving group that that does not interfere with olefin cross metathesis, $R^{34}$ and $R^{35}$ are each independently hydrogen, a non-acyl alcohol protecting group, or an acyl group, G is hydrocarbylene linker group comprising 6–30 carbon atoms, wherein the carbon atoms of the linker group may be substituted or unsubstituted and the linker group may be interrupted by up to 6 hetero atoms selected from O, S and N, and wherein two or more substituents on the chain may be linked to form an additional cyclic group, $X^6$ is a one-atom, two-atom, three-atom, four-atom or five atom linkage, y is an integer from 0 to 4, and $R^{27}$ in each occurrence may replace a hydrogen atom on a ring carbon and each occurrence is independently selected from hydrocarbyl, substituted hydrocarbyl, heteroatom-containing hydrocarbyl, substituted heteroatom-containing hydrocarbyl, and -(L)$_v$-Fn wherein v is zero or 1, L is hydrocarbylene, substituted hydrocarbylene and/or heroatom-containing hydrocarbylene, and Fn is a functional group, wherein two $R^{27}$ groups may collectively form a carbonyl group.

* * * * *